US012740951B2

(12) United States Patent
Meghpara et al.

(10) Patent No.: US 12,740,951 B2
(45) **Date of Patent: *Sep. 22, 2026**

(54) DELAYED RELEASE COMPOSITIONS

(71) Applicant: AMNEAL COMPLEX PRODUCTS RESEARCH LLC, Bridgewater, NJ (US)

(72) Inventors: Kanji Meghpara, Morris Plains, NJ (US); Siva Ram Kiran Vaka, Piscataway, NJ (US); Dipen Desai, Whippany, NJ (US); Navnit H. Shah, Monmouth Junction, NJ (US)

(73) Assignee: Amneal Complex Products Research LLC, Bridgewater, NJ (US)

( * ) Notice: Subject to any disclaimer, the term of this patent is extended or adjusted under 35 U.S.C. 154(b) by 1036 days.

This patent is subject to a terminal disclaimer.

(21) Appl. No.: 17/470,335

(22) Filed: Sep. 9, 2021

(65) Prior Publication Data

US 2022/0079896 A1 Mar. 17, 2022

Related U.S. Application Data

(60) Provisional application No. 63/077,276, filed on Sep. 11, 2020.

(51) Int. Cl.

*A61K 31/165* (2006.01)
*A61K 9/00* (2006.01)
*A61K 9/20* (2006.01)
*A61K 9/28* (2006.01)

(52) U.S. Cl.

CPC .......... *A61K 31/165* (2013.01); *A61K 9/0004* (2013.01); *A61K 9/2031* (2013.01); *A61K 9/2086* (2013.01); *A61K 9/2095* (2013.01); *A61K 9/2866* (2013.01)

(58) Field of Classification Search

CPC .. A61K 31/165; A61K 9/0004; A61K 9/2031; A61K 9/2086; A61K 9/2095; A61K 9/2866

See application file for complete search history.

(56) References Cited

U.S. PATENT DOCUMENTS 5,156,850 A * 10/1992 Wong .................. A61K 9/0004 424/473
6,004,582 A * 12/1999 Faour ........................ A61P 7/00 424/473
7,132,570 B2 11/2006 Neckebrock et al.
7,297,346 B2 11/2007 Corvari et al.
7,521,067 B1 4/2009 Greerke et al.
8,153,159 B2 4/2012 Parikh et al.
10,980,738 B2 * 4/2021 Vaka .................. A61K 31/4178
11,000,471 B2 * 5/2021 Vaka .................... A61K 31/137
11,154,494 B2 * 10/2021 Vaka .................... A61K 31/135
11,166,906 B2 * 11/2021 Vaka .................... A61K 31/137
2001/0012847 A1 * 8/2001 Lam ................... A61K 31/4422 514/317
2005/0095295 A1 * 5/2005 Maggi .................. A61K 9/2072 424/472
2010/0112052 A1 5/2010 Chen et al.
2020/0405626 A1 * 12/2020 Vaka .................. A61K 31/4458
2021/0030685 A1 * 2/2021 Vaka .................. A61K 31/4458
2021/0205207 A1 * 7/2021 Vaka .................... A61K 9/2031
2021/0228474 A1 * 7/2021 Vaka .................. A61K 31/4168
2021/0393512 A1 * 12/2021 Vaka .................. A61K 31/4178

FOREIGN PATENT DOCUMENTS

EP 0768867 4/1997
WO WO 1995/34285 12/1995
WO WO 99/62496 12/1999
WO WO-2019173384 A1 * 9/2019 ........... A61K 31/135

OTHER PUBLICATIONS

Rosen et al. The rise and rise of drug delivery. Nature Reviews Drug Discovery | AOP, published online Apr. 22, 2005. 5 pages (Year: 2005).*
Kurlan R, et al., Clonidine and methylphenidate were effective for attention deficit hyperactivity disorder in children with comorbid tics, Evidence-based medicine, BMJ Group, UK, US, vol. 7, No. 5, Sep. 1, 2002, p. 157 XP002724188, ISSN: 1356-5524, DOI: 10.1136/EBM.7.5.157.
Robinson, et al., The osmotic coefficients of some organic compounds in relation to their chemical constitution, Trans. Faraday Soc., vol. 38, Jan. 1, 1942, pp. 63-70, XP5589305, Figure 1, table V.

* cited by examiner

*Primary Examiner* — Robert A Wax
*Assistant Examiner* — Olga V. Tcherkasskaya
(74) *Attorney, Agent, or Firm* — Amneal Complex Products Research LLC; Vandana Awasthi

(57) ABSTRACT

The present disclosure provides oral compositions providing delayed release of armodafinil/modafinil. The compositions of the disclosure provide a lag time that is independent of the presence or absence of food, type of food, pH, gastric emptying, gastric motility, and volume and viscosity of gastric fluid. The compositions of the disclosure can be programmed to provide a desired lag time, and release drug at a rhythm that matches the human circadian rhythm regulating sleep-wake cycle to optimize therapeutic outcome and minimize side effects.

18 Claims, 3 Drawing Sheets

DELAYED RELEASE COMPOSITIONS

1. RELATED APPLICATIONS

Figure 1:
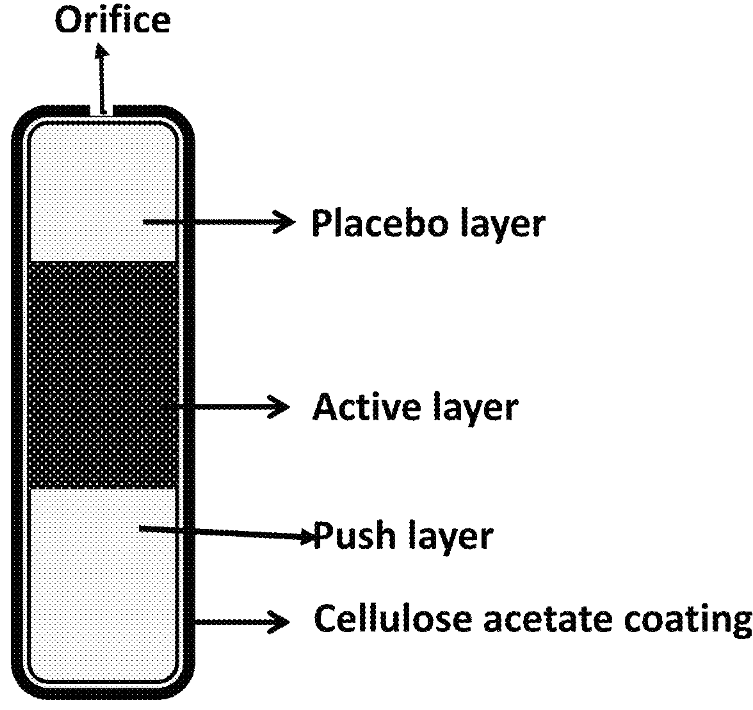

This application claims priority to U.S. Provisional Patent Application No. 63/077,276, filed Sep. 11, 2020, the disclosure of which is hereby incorporated by reference in its entirety.

2. TECHNICAL FIELD

The presently disclosed subject matter relates to oral compositions providing delayed release of armodafinil or a pharmaceutically acceptable salt thereof. The compositions of the disclosure can be programmed to provide a desired lag time, thereby releasing the drug (e.g., armodafinil or a pharmaceutically acceptable salt thereof) after the lag time, at a rhythm, that matches the human circadian rhythm regulating sleep-wake cycle. The compositions of the disclosure can be administered at night (e.g., before bedtime) and the drug release is delayed, providing a desired lag time for at least about 4 hours, e.g., for about 6 to about 10 hours or longer, to provide therapeutic plasma concentrations of the drug, even while releasing the drug in the lower portions of the GI tract.

3. BACKGROUND

R enantiomer of modafinil, also known as armodafinil, has the chemical name (−)-2-[(R)-(diphenylmethyl) sulfinyl] acetamide, and the following chemical structure:

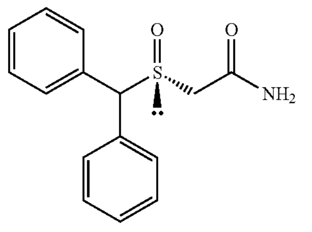

Armodafinil is commercially available as NUVIGIL® and has been approved for improving wakefulness in adult patients with excessive sleepiness associated with obstructive sleep apnea (OSA), narcolepsy, or shift work disorder (SWD). Armodafinil is well tolerated and has the safety profile comparable to modafinil. Armodafinil and modafinil both have a mean single-dose terminal elimination half-life of approximately 13 hours. One major challenge of improving wakefulness in adult patients on armodafinil is delivering and maintaining an effective drug concentration in patients throughout the day, in particular during the morning hours to reduce/treat sleep inertia/sleep drunkenness, a condition which impairs ability to wake up for school and work. Typically, Armodafinil is administered once a day in the morning or one hour prior to the work shift. However, patients with sleep inertia/sleep drunkenness experience extreme or prolonged difficulty fully awakening and getting out of bed in the morning, a transition state between sleep and wake marked by impaired performance, reduced vigilance, and desire to return to sleep.

For at least these reasons, there remains a need to develop oral delayed release compositions of armodafinil/modafinil that can be administered before bedtime to provide delayed release of the drug in early morning, while maintaining therapeutic plasma concentration of the drug throughout the day. The present disclosure addresses the above-mentioned unmet needs in the art by providing oral delayed release armodafinil/modafinil compositions that can improve the symptoms of a disease in the early morning and throughout the day, without the need for early morning dosing. Although suitable for providing a controlled release of drugs with various solubilities, osmotic-controlled compositions known in the art are not entirely suitable for being programmed as compositions that 1) delay the release of a drug/provide a lag time for at least about 4 hours, 2) provide a plasma concentration of the drug/active pharmaceutical ingredient during the lag time that is less than about 20% of a maximum concentration ($C_{max}$), 3) provide drug release at a rhythm that matches the human circadian rhythm regulating sleep-wake cycle, and 4) provide a desired bioavailability and substantially complete drug recovery at a desired time.

The present disclosure addresses the above-mentioned unmet needs in the art by providing unique oral delayed release compositions that can avoid burdensome early morning dosing and can be programmed to provide a desired lag time, thereby releasing the drug at a rhythm, that matches the human circadian rhythm regulating sleep-wake cycle, to optimize therapeutic outcome and minimize side effects. The compositions of the disclosure provide a lag time that is substantially independent of the presence or absence of food, type of food, pH, gastric emptying, gastric transit time, and volume of fluid in the immediate microenvironment of drug release. In particular, the oral, delayed release compositions of the disclosure provide desired drug bioavailability, despite releasing the drug in lower portions of the GI tract, e.g., colon, with viscous alkaline microenvironment. The oral compositions of the disclosure are designed to provide minimal variability in drug release among tablets.

4. SUMMARY

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

To achieve these advantages and in accordance with the purpose of the disclosed subject matter as embodied and broadly described, the disclosed subject matter includes a delayed release composition comprising a multilayer core and a semipermeable membrane comprising an orifice and surrounding the core. The multilayer core comprises a placebo layer, an active layer, and a push layer, wherein the placebo layer comprises at least one polyethylene oxide polymer having an average molecular weight of from about 400,000 Da to about 900,000 Da; the active layer comprises an active agent comprising armodafinil or a pharmaceutically acceptable salt thereof, and at least one polyethylene oxide polymer having an average molecular weight of from about 100,000 Da to about 300,000 Da; and the push layer comprises at least one polyethylene oxide polymer having an average molecular weight of greater than or equal to 1000,000 Da. The layers in the multilayer core are placed in the following order: the placebo layer in fluid communication with the orifice in the semipermeable membrane; the active layer; and the push layer facing away from the orifice.

In certain embodiments, the push layer further comprises an osmogen. In certain embodiments, the osmogen is present in an amount of from about 10 w % to about 60 wt. %, based on total weight of the push layer.

In certain embodiments, the composition provides a lag time of at least 4 hours during which the composition releases no more than 10% of the active agent, followed by release of the active agent. In certain embodiments, the composition provides a lag time of at least about 6 hours, during which the composition releases no more than 10 wt. % of the active agent.

In certain embodiments, the composition exhibits not more than 30% variability in the lag time with variations in pH, viscosity, and volume of a dissolution medium. In certain embodiments, the lag time does not depend upon gastric motility and presence of food in the GI tract.

In certain embodiments, the semipermeable membrane is present in an amount of from about 1 wt. % to about 30 wt. % coating weight gain, based on the total weight of the uncoated multilayer core.

In certain embodiments, the semipermeable membrane comprises at least one water-insoluble polymer and at least one water-soluble pore former at a polymer to pore former weight ratio of between about 70:30 and about 99.5:0.5. In certain embodiments, the semipermeable membrane comprises a polymer to pore former weight ratio of between about 80:20 and about 95:5. In certain embodiments, the water-insoluble polymer is selected from the group consisting of cellulose acetate, cellulose acetate butyrate, and cellulose triacetate. In certain embodiments, the pore former is selected from the group consisting of polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

In certain embodiments, the semipermeable membrane comprises at least water-insoluble polymer and at least one plasticizer. In certain embodiments, the plasticizer is selected from the group consisting of polyethylene glycols, triethyl citrate, triacetin, diethyl tartrate, dibutyl sebacate, and combinations thereof.

In certain embodiments, the polyethylene oxide polymer in the push layer has an average molecular weight of about 1000,000 Da, about 2000,000 Da, about 4000,000 Da, about 5000,000 Da, about 7000,000 Da, or intermediate values therein.

In certain embodiments, the active layer comprises a weight ratio of the active agent:polyethylene oxide polymer of from about 50:50 to about 95:5. In certain embodiments, the active agent is armodafinil or a pharmaceutically acceptable salt thereof.

In certain embodiments, each of the push layer, the placebo layer, and the active layer exhibit a viscosity, measured using Brookfield viscometer, in 1% aqueous solution at 25° C., wherein the viscosity of the push layer >the viscosity of the placebo layer >the viscosity of the active layer.

In certain embodiments, the disclosure provides a method for treating excessive sleep disorder in patients suffering from narcolepsy, obstructive sleep apnea, shift work sleep disorders, or idiopathic hypersomnia, the method comprising orally administering to the patient, a delayed release composition comprising a multilayer core and a semipermeable membrane comprising an orifice and surrounding the core. The multilayer core comprises a placebo layer, an active layer, and a push layer, wherein the placebo layer comprises at least one polyethylene oxide polymer having an average molecular weight of from about 400,000 Da to about 900,000 Da; the active layer comprises an active agent comprising armodafinil or a pharmaceutically acceptable salt thereof, and at least one polyethylene oxide polymer having an average molecular weight of from about 100,000 Da to about 300,000 Da; and the push layer comprises at least one polyethylene oxide polymer having an average molecular weight of greater than or equal to 1000,000 Da. The layers in the multilayer core are placed in the following order: the placebo layer in fluid communication with the orifice in the semipermeable membrane; the active layer; and the push layer facing away from the orifice.

In certain embodiments, the push layer further comprises an osmogen. In certain embodiments, the osmogen is present in an amount of from about 10 w % to about 60 wt. %, based on total weight of the push layer.

In certain embodiments, the composition provides a lag time of at least 4 hours during which the composition releases no more than 10% of the active agent, followed by release of the active agent.

In certain embodiments, the active agent is armodafinil or a pharmaceutically acceptable salt thereof.

In certain embodiments, each of the push layer, the placebo layer, and the active layer exhibit a viscosity, measured using Brookfield viscometer, in 1% aqueous solution at 25° C., wherein the viscosity of the push layer >the viscosity of the placebo layer >the viscosity of the active layer.

In certain embodiments, the disclosure provides a method for treating excessive sleep disorder in patients suffering from narcolepsy. In certain embodiments, the disclosure provides a method for treating excessive sleep disorder in patients suffering from obstructive sleep apnea.

In certain embodiments, the disclosure provides a method for treating excessive sleep disorder in patients suffering from shift work sleep disorders. In certain embodiments, the disclosure provides a method for treating excessive sleep disorder in patients suffering from idiopathic hypersomnia.

In certain embodiments, the disclosure provides a method for improving early morning wakefulness in patients suffering from narcolepsy, obstructive sleep apnea, shift work sleep disorders, or idiopathic hypersomnia, the method comprising orally administering to the patient, a delayed release composition comprising a multilayer core and a semipermeable membrane comprising an orifice and surrounding the core. The multilayer core comprises a placebo layer, an active layer, and a push layer, wherein the placebo layer comprises at least one polyethylene oxide polymer having an average molecular weight of from about 400,000 Da to about 900,000 Da; the active layer comprises an active agent comprising armodafinil or a pharmaceutically acceptable salt thereof, and at least one polyethylene oxide polymer having an average molecular weight of from about 100,000 Da to about 300,000 Da; and the push layer comprises at least one polyethylene oxide polymer having an average molecular weight of greater than or equal to 1000,000 Da. The layers in the multilayer core are placed in the following order: the placebo layer in fluid communication with the orifice in the semipermeable membrane; the active layer; and the push layer facing away from the orifice.

In certain embodiments, the push layer further comprises an osmogen. In certain embodiments, the osmogen is present in an amount of from about 10 w % to about 60 wt. %, based on total weight of the push layer.

In certain embodiments, the composition provides a lag time of at least 4 hours during which the composition releases no more than 10% of the active agent, followed by release of the active agent.

In certain embodiments, the active agent is armodafinil or a pharmaceutically acceptable salt thereof.

In certain embodiments, each of the push layer, the placebo layer, and the active layer exhibit a viscosity, measured using Brookfield viscometer, in 1% aqueous solution at 25° C., wherein the viscosity of the push layer >the viscosity of the placebo layer >the viscosity of the active layer.

In certain embodiments, the disclosure provides a method for improving early morning wakefulness in patients suffering from narcolepsy. In certain embodiments, the disclosure provides a method improving early morning wakefulness in patients suffering from obstructive sleep apnea. In certain embodiments, the disclosure provides a method for improving early morning wakefulness in patients suffering from shift work sleep disorders. In certain embodiments, the disclosure provides a method for improving early morning wakefulness in patients suffering from idiopathic hypersomnia.

In certain embodiments, the disclosure provides a method for treating excessive sleep disorder and improving early morning wakefulness in patients suffering from narcolepsy, obstructive sleep apnea, shift work sleep disorders, or idiopathic hypersomnia, the method comprising orally administering to the patient, a delayed release composition comprising a multilayer core and a semipermeable membrane comprising an orifice and surrounding the core. The multilayer core comprises a placebo layer, an active layer, and a push layer, wherein the placebo layer comprises at least one polyethylene oxide polymer having an average molecular weight of from about 400,000 Da to about 900,000 Da; the active layer comprises an active agent comprising armodafinil or a pharmaceutically acceptable salt thereof, and at least one polyethylene oxide polymer having an average molecular weight of from about 100,000 Da to about 300,000 Da; and the push layer comprises at least one polyethylene oxide polymer having an average molecular weight of greater than or equal to 1000,000 Da. The layers in the multilayer core are placed in the following order: the placebo layer in fluid communication with the orifice in the semipermeable membrane; the active layer; and the push layer facing away from the orifice.

In certain embodiments, the push layer further comprises an osmogen. In certain embodiments, the osmogen in the push layer is present in an amount of from about 10 w % to about 60 wt. %, based on total weight of the push layer.

In certain embodiments, the composition provides a lag time of at least 4 hours during which the composition releases no more than 10% of the active agent, followed by release of the active agent.

In certain embodiments, the active agent is armodafinil or a pharmaceutically acceptable salt thereof.

In certain embodiments, each of the push layer, the placebo layer, and the active layer exhibit a viscosity, measured using Brookfield viscometer, in 1% aqueous solution at 25° C., wherein the viscosity of the push layer >the viscosity of the placebo layer >the viscosity of the active layer.

In certain embodiments, the method comprises treating excessive sleep disorder and improving early morning wakefulness in patients suffering from narcolepsy. In certain embodiments, the method comprises treating excessive sleep disorder and improving early morning wakefulness in patients suffering from obstructive sleep apnea. In certain embodiments, the method comprises treating excessive sleep disorder and improving early morning wakefulness in patients suffering from shift work sleep disorders. In certain embodiments, the method comprises treating excessive sleep disorder and improving early morning wakefulness in patients suffering from idiopathic hypersomnia.

In certain embodiments, the disclosure provides a method for making a delayed release composition comprising a multilayer core comprising a placebo layer comprising a placebo layer blend; an active layer comprising an active layer blend; and a push layer comprising a push layer blend; and a semipermeable membrane covering at least a portion of the multilayer core and comprising at least one orifice. The method comprises (i) making a placebo layer blend comprising at least one polyethylene oxide polymer having an average molecular weight of from about 400,000 Da to about 900,000 Da; (ii) making an active layer blend comprising an active agent comprising armodafinil or a pharmaceutically acceptable salt thereof, and at least one polyethylene oxide polymer having an average molecular weight of from about 100,000 Da to about 300,000 Da; (iii) making a push layer blend comprising at least one polyethylene oxide polymer having an average molecular weight of greater than or equal to 1000,000 Da, and at least one osmogen; (iv) compressing the placebo layer blend, the active layer blend, and the push layer blend into a multilayer core comprising a placebo layer, an active layer, and a push layer; (v) coating the trilayer tablet core with a semipermeable membrane coat; and (vi) laser drilling an orifice in the semipermeable membrane coat. The layers in the multilayer core are placed in the following order: the placebo layer in fluid communication with the orifice in the semipermeable membrane; the active layer; and the push layer facing away from the orifice.

In certain embodiments, the placebo layer blend comprises placebo layer granules comprising the polyethylene oxide polymer with an average molecular weight of from about 400,0000 Da to about 900,0000 Da.

In certain embodiments, the active layer blend comprises active layer granules comprising the polyethylene oxide polymer with an average molecular weight of from about 100,0000 Da to about 300,0000 Da.

In certain embodiments, the push layer blend comprises push layer granules comprising the polyethylene oxide polymer with an average molecular weight of greater than or equal to 1000,000 Da.

In certain embodiments, the granules are made via wet granulation.

5. BRIEF DESCRIPTION OF THE DRAWINGS

FIG. 1 depicts a cross-section view of a three-layer dosage form comprising a cellulose acetate coating comprising an orifice; a placebo layer facing the orifice; an active layer comprising armodafinil or a pharmaceutically acceptable salt thereof, placed below the placebo layer; and a push layer placed below the active layer.

Figure 2:
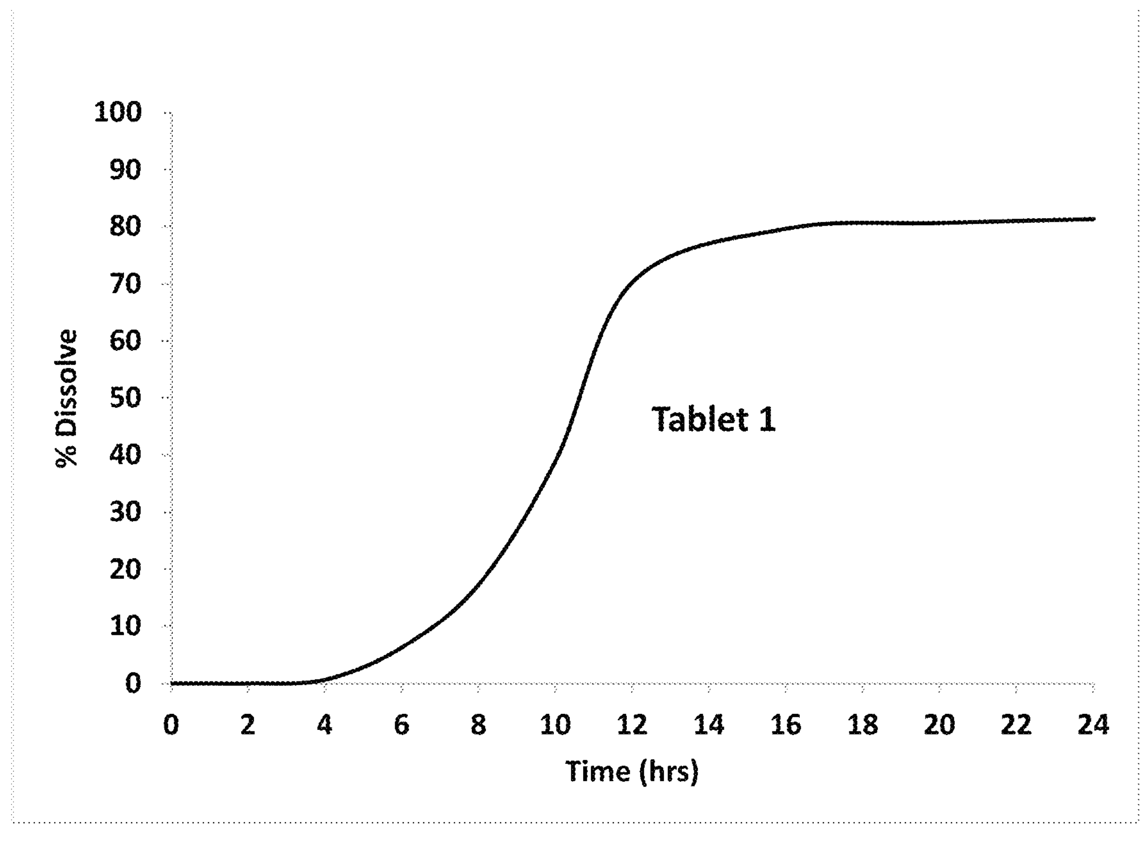

FIG. 2 shows dissolution profile of one of Tablet 1, placed in a dissolution medium comprising pH 6.8 phosphate buffer, using USP II (Paddle) at about 50 rpm and about 37° C. Percent drug dissolved is plotted over time (hours). The figure demonstrates that the composition delays the release of armodafinil by at least about 4 hours, e.g., about 6 hours, during which the composition releases no more than 10% of the total amount of armodafinil present in the tablet.

Figure 3:
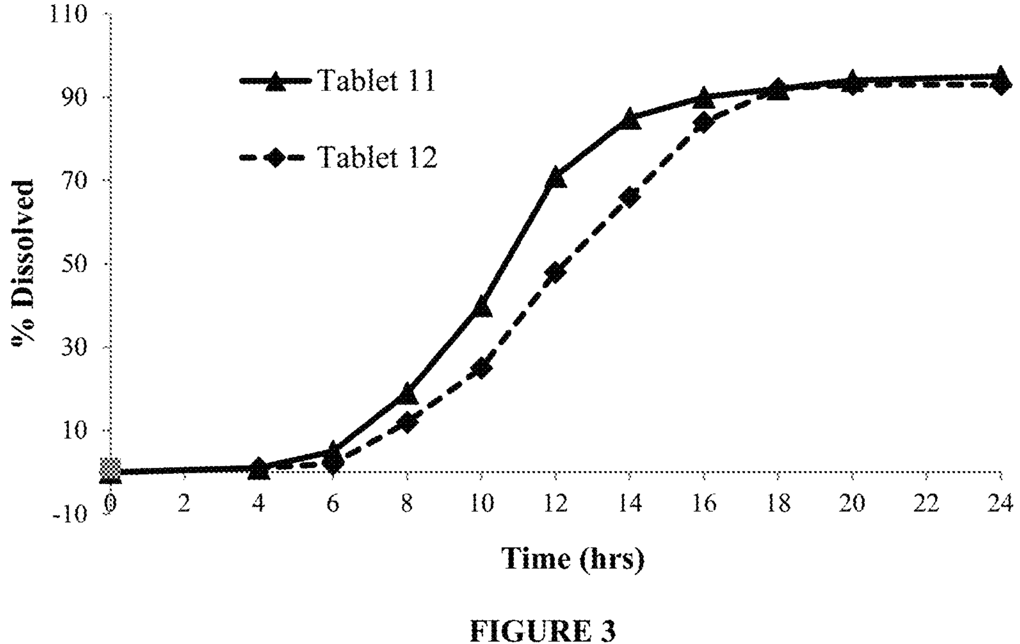

FIG. 3 compares dissolution profiles of one of Tablets 11 and 12, placed in a dissolution medium comprising pH 6.8 phosphate buffer, using USP II (Paddle) at about 50 rpm and about 37° C. Percent drug dissolved is plotted over time (hours). The figure demonstrates that Tablets 11 (6% coating wt. gain) and 12 (8% coating wt. gain) provide a lag time of at least about 6 hours during which not more than 10% of armodafinil is released. The figure further demonstrates that Tablet 11 with 6% coating wt. gain provided faster drug release compared to Tablet 12 with 8% coating wt. gain.

6. DETAILED DESCRIPTION

The present disclosure is directed to delayed release armodafinil compositions, amongst other things.

6.1. Definitions

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

The terminology used in the present disclosure is for the purpose of describing particular embodiments only and is not intended to be limiting.

As used herein, the use of the word "a" or "an" when used in conjunction with the term "comprising" in the claims and/or when used in the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items.

The term "about" or "approximately" means within an acceptable error range for the particular value as determined by one of ordinary skill in the art, which will depend in part on how the value is measured or determined, i.e., the limitations of the measurement system. Alternatively, "about" can mean a range of up to 20%, up to 15%, up to 10%, up to 5%, up to 1%, up to 0.5%, or even up to 0.1% of a given value.

As used herein, a "therapeutically effective," "therapeutic," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject.

As used herein, the term "drug recovery" refers to percentage of drug (based on the total amount of drug present in the dosage form) released in a dissolution medium. The term "complete drug recovery" refers to release of about 80% to about 105% of the drug, based on the total amount of drug present in the dosage form.

The term "bioavailability" refers to the fraction of an administered dose of unchanged drug that reaches the systemic circulation.

As used herein, the terms "treatment," "treat," and "treating" refer to reversing, alleviating, delaying the onset of, and/or inhibiting the progress of a disease or disorder as described herein.

In some embodiments, treatment can be administered after one or more symptoms have developed. In other embodiments, treatment can be administered in the absence of symptoms.

For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

The term "chrono release" refers to drug release in a sequential order of time. In particular, the term "chrono release" means timed or programmed release of one or more drugs at a rhythm that matches the human circadian rhythm of a condition's symptoms and/or of the individual being treated in the application of the therapy to optimize the therapeutic outcome and minimize side effects.

The term "lag time" means the time for which release of a drug/active agent is delayed from the time of administration/ingestion of the composition. Not more than about 20 wt. % of the maximum plasma concentration ($C_{max}$) of the drug is released during the lag time.

The term "release rate" refers to the quantity of drug released per unit time, e.g., mg of drug released per hour (mg/hour), from a dosage form. Drug release rates are calculated under in vitro dosage form dissolution testing conditions known in the art.

The term "delayed release" means release of a drug at a time(s) other than immediately after administration/ingestion.

The term "immediate release" means substantially complete release of a drug within about 1 hour or less, preferably within 30 minutes or less, post-administration.

The terms "gastric fluid," and "GI fluid," as used interchangeably herein, refer to medium occurring in the stomach and lower gastrointestinal tract of an individual.

The terms "simulated gastric fluid," and "SGF," as used interchangeably herein, refers to a medium that is used to mimic the chemical environment of gastric fluid/medium in an in vitro setting.

The term "dissolution medium," as used herein, refers to an aqueous medium used to mimic pH of gastric fluid/medium in stomach or lower gastrointestinal tract of an individual. In certain embodiments, the medium used to mimic chemical environment of stomach of an individual includes a medium with pH of less than about 5.5, e.g., about 1, about 1.25, about 1.5, about 1.75, about 2, about 2.25, about 2.5, about 2.75, about 3, about 3.25, about 3.5, about 3.75, about 4.0, about 4.25, about 4.5, about 4.75, about 5.0, about 5.5, or any intermediate values therein.

In certain embodiments, the medium used to mimic chemical environment of lower GI tract of an individual includes a medium with pH of from about 5.5 to about 8, e.g., about 5.5, about 5.75, about 6.0, about 6.25, pH 6.5, about 6.75, about 7, about 7.25, about 7.5, or any intermediate values therein.

The terms "viscosity," "viscosity in aqueous medium," and "viscosity on imbibition of aqueous medium," as used interchangeably herein, refer to viscosities of placebo layer, active layer, and/or push layer, measured using Brookfield viscometer, in 1 wt % aqueous medium, e.g., purified water, at a temperature of about 25° C. Viscosity is measured as force per unit area resisting a flow in which parallel layers unit distance apart have unit speed relative to one another.

The term "average molecular weight," as used herein with respect to the polyethylene oxide polymers, refers to weight average molecular weight.

The term "osmosis" refers to a spontaneous movement of a solvent from a solution of lower solute concentration to a solute or a solution of higher solute concentration through a semipermeable membrane, wherein the membrane is substantially impermeable to passage of solutes, and substantially permeable to passage of fluids.

The term "osmotic pressure" refers to a pressure exerted on a higher solvent concentration side of the dosage form to inhibit solvent flow into the dosage form.

The terms "semipermeable membrane," and "functional coat," as used interchangeably herein, refer to a membrane/coat/film that is substantially impermeable to the passage of drug/active agent. In certain embodiments, the membrane/coat/film that is substantially impermeable to passage of active agent and excipients, and substantially permeable to passage of fluids.

The terms "pore former" and the like, as used herein, refer to water-soluble polymers and/or water-soluble small molecules that will form pores or channels (i.e., behave as a channeling agent) in a semipermeable membrane to improve permeability of the membrane. In certain embodiments, the pore former is pH independent. In certain embodiments, the pore former is pH dependent.

The terms "orifice," "hole", and "delivery port," as used interchangeably herein, refer to an opening/exit means in coatings, e.g., in the semipermeable membrane coat, the seal coat, and/or the overcoat, of an osmotic-controlled composition facing the placebo layer. The appropriate opening can be formed by any means, e.g., by manual or laser drilling of the membrane. In certain embodiments, the semipermeable membrane facing the top of the placebo layer is completely removed to provide an orifice comprising an optimum diameter that is equivalent to the diameter of the top of the placebo layer end of the multilayer core. In certain embodiments, the optimum orifice diameter is from about 0.1 mm and about 1.5 mm.

The term "coating weight gain", as used herein, refers to coating weight gain with respect to the weight of the uncoated tablet. For example, a coating weight gain of 15% refers to a 15 wt. % increase in tablet weight during coating with respect to the uncoated tablet weight.

The terms "obstructive sleep apnea" and "OSA," as used interchangeably herein, refer to a common disorder characterized by repetitive episodes of nocturnal breathing cessation due to upper airway collapse.

The term "idiopathic hypersomnia," as used herein, refers to chronic neurological sleep disorder characterized by excessive daytime sleepiness and often difficulty waking up (sleep inertia) from nocturnal sleep or daytime naps.

The terms "sleep inertia," and "sleep drunkenness," as used interchangeably herein, refer to extreme or prolonged difficulty fully awakening and getting out of bed in the morning. Sleep inertia/sleep drunkenness can be a transition state between sleep and wake marked by impaired performance, reduced vigilance, and desire to return to sleep. Sleep inertia is a common symptom of Idiopathic hypersomnia.

The term "cataplexy," as used herein, refers to sudden episodes of muscle paralysis.

The terms "hypersomnolence," and "daytime sleepiness," as used interchangeably as used herein, refer to a condition wherein a person experiences significant episodes of sleepiness, even after 7 hours or more of quality sleep.

The term "substantially free", as used herein, refers to excluding any functional (e.g., noncontaminating) amount, i.e., any amount that contributes or has an effect on release profile or lag time of the composition. In certain embodiments, the term refers to an amount comprising less than 0.1 wt. %, e.g., less than 0.01 wt %, of a material.

The terms "shear" and "shear effect," as used interchangeably herein, refer to peristaltic waves, particularly under fed conditions, moving from the mid-corpus of the stomach to the pylorus. In certain embodiments, dissolution methods comprise dissolution using USP Apparatus II (Paddle) at 50 rpm and 37° C.

The term "osmotic agent" as used herein, refers to swellable hydrophilic polymers, and osmogens/ionic compounds consisting of inorganic salts.

The term "wicking agent" as used herein, refers to a material with the ability to draw/spread water into the porous network of the osmotic composition. The wicking agent helps to increase the contact surface area of the drug with the incoming aqueous fluid.

The term "patient," "person in need thereof," or "subject," as used herein, refers to a human or nonhuman mammal that is in need or may be in need to receive dosage forms of the present disclosure.

The terms "drug," "active agent," "active ingredient," and "active pharmaceutical ingredient/agent" are used interchangeably herein and include compounds that will elicit a therapeutically useful response in a subject; such terms include all polymorphs, prodrugs, solvates, hydrates, pharmaceutically acceptable salts, esters, and functionally equivalent chemical compounds. In certain embodiments, the term "drug" is used interchangeable with "armodafinil or a pharmaceutically acceptable salt thereof" The term "armodafinil" includes all pharmaceutically acceptable salts, polymorphs, solvates, hydrates, esters, and functionally equivalent chemical compounds.

The term "modafinil" includes all pharmaceutically acceptable salts, polymorphs, solvates, hydrates, esters, and functionally equivalent chemical compounds.

6.2 Multi-Layer Tablet Core

The present disclosure provides delayed release oral compositions comprising a multilayer core (e.g., a trilayer tablet core) comprising an active agent, e.g., armodafinil, modafinil, or pharmaceutically acceptable salts thereof, wherein the core is coated with a semipermeable membrane comprising at least one orifice. The multilayered tablet core comprises a pull layer containing the active agent, and a push layer. The pull layer comprises at least two layers: a placebo layer, for providing a desired lag time for the release of the active agent; and an active layer containing the active agent and providing delayed release of the active agent. In certain embodiments, the active agent is armodafinil or a pharmaceutically acceptable salt thereof. In certain embodiments, the active agent is modafinil or a pharmaceutically acceptable salt thereof.

In certain embodiments, the membrane comprises multiple orifices. In certain embodiments, the at least one orifice is present on the placebo layer side of the multilayer tablet core. In certain embodiments, the layers are vertically compressed producing a capsule-shaped product. In certain embodiments, such shape ensures complete extrusion of drug from the orifice.

For any of the compositions, and methods of the disclosure, the push layer is present in an amount that expands in volume to a size that pushes substantially all of the pull layer, comprising the placebo layer, and the active layer comprising the drug, e.g., armodafinil/modafinil or pharmaceutically acceptable salts thereof, out of the composition through a delivery port/orifice, thereby providing, e.g., substantially complete drug recovery from the composition. In certain embodiments, the pull layer and the push layer are present in a ratio of from about 5:1 to about 1:1, e.g., about 5:1, about 4.5:1, about 4:1, about 3.5:1, about 3:1, about 2.5:1, about 2:1, about 1.5:1, about 1:1, or any intermediate values therein. In certain embodiments, the weight of the placebo layer is from about 10 wt. % to about 40 wt. %, based on the total weight of the trilayer core. In certain embodiments, the weight of the placebo layer is about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, or about 40 wt. %, based on the total weight of the trilayer core. In certain embodiments, the weight of the active layer is from about 20 wt. % to about 70 wt. %, based on the total weight of the trilayer core. In certain embodiments, the weight of the active layer is about 20 wt. %, about 25 wt. %, about 30 wt. %, about 35 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about wt. %, about 69 wt. %, or about 70 wt. %, based on the total weight of the trilayer core. In certain embodiments, the weight of the push layer is from about 10 wt. % to about 40 wt. %, based on the total weight of the trilayer core. In certain embodiments, the weight of the push layer is about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, or about 40 wt. %, based on the total weight of the trilayer core.

Furthermore, each of the layers, i.e., the active layer, the placebo layer, and the push layer, can comprise at least one polyethylene oxide polymer (e.g., sold under the trademark) POLYOX®). In certain embodiments, average molecular weight of the polyethylene oxide polymer in each of the placebo layer, active layer, and push layer determines the viscosity of the corresponding layer in aqueous medium. In certain embodiments, the polyethylene oxide polymer in the placebo layer has an average molecular weight from about 300,000 Da to about 900,000 Da, e.g., about 400,000 Da (e.g., sold under the trademark POLYOX® WSR N 301), about 600,000 Da (e.g., sold under the trademark POLYOX® WSR 205) or about 900,000 Da (e.g., sold under the trademark POLYOX® WSR 1105). In certain embodiments, the polyethylene oxide polymer in the active layer has an average molecular weight of from about 100,000 Da (e.g., sold under the trademark POLYOX® WSR N-10) to about 300,000 Da (e.g., sold under the trademark POLYOX® WSR N-750); or about 200,000 Da (e.g., sold under the trademark POLYOX® WSR N-80). In certain embodiments, the polyethylene oxide polymer in the push layer has an average molecular weight of ≥ 1000,000 Da (e.g., sold under the trademark POLYOX® WSR N 12K), about 2000,000 Da (e.g., sold under the trademark POLYOX® WSR N 60K), about 4000,000 Da (e.g., sold under the trademark POLYOX® WSR 301), about 5000,000 Da (e.g., sold under the trademark POLYOX® WSR Coagulant), about 7000,000 Da (e.g., sold under the trademark POLYOX® WSR 303).

In certain embodiments, viscosity of the placebo layer in aqueous medium, e.g., after imbibition of aqueous medium, depends upon the average molecular weight/grade of the polyethylene oxide polymer present in the placebo layer. In certain embodiments, viscosity of the placebo layer in aqueous medium, increases with increasing average molecular weight of the polyethylene oxide polymer present in the placebo layer. In certain embodiments, the lag time increases with increasing the molecular weight/grade of the polyethylene oxide polymer present in the placebo layer. In certain embodiments, the volume of the placebo layer depends upon the amount of polyethylene oxide polymer present in the placebo layer.

In certain embodiments, the average molecular weight of the polyethylene oxide polymer present in the placebo layer is higher than the average molecular weight of the polyethylene oxide polymer present in the active layer, and viscosity of the placebo layer is higher than the viscosity of the active layer, measured using Brookfield viscometer in 1 wt % aqueous solution at 25° C. In certain embodiments, the average molecular weight of the polyethylene oxide polymer present in the push layer higher than the average molecular weight of the polyethylene oxide polymer present in the placebo layer, and the average molecular weight of the polyethylene oxide polymer present in the placebo layer is higher than the average molecular weight of the polyethylene oxide polymer present in the active layer. In certain embodiments, viscosity of the push layer is higher than the viscosity of the placebo layer, and the viscosity of the placebo layer is higher than the viscosity of the active layer, measured using Brookfield viscometer, in 1 wt % aqueous medium at about 25° C.

In certain embodiments, the placebo layer, the active layer, and/or the push layer comprise at least one osmogen. In certain embodiments, the placebo layer and/or the active layer comprise at least one wicking agent. In certain embodiments the presence of osmogen and/or wicking agents in the placebo layer are optional. In certain embodiments the presence of osmogen and/or wicking agents in the active layer are optional. In certain embodiments, the push layer does not include any wicking agent. In certain embodiments, viscosity in aqueous medium, of each of the placebo layer, the active layer, and the push layer, is not substantially altered, e.g., has no effect on release profile and lag time of the composition, by the presence of osmogen, wicking agent, surfactant, lubricant, and glidant, when present alone or in combination.

In certain embodiments, the placebo layer and the push layer are free of active agent, e.g., armodafinil/modafinil or pharmaceutically acceptable salts thereof. In certain embodiments, active agent contained in the active layer does not leach/migrate into the placebo layer or the push layer during the in vitro drug release test. In certain embodiments, less that about 20 wt. %, less than about 19 wt. %, less than about 18 wt. %, less than about 17 wt. %, less than about 16 wt. %, less than about 15 wt. %, less than about 14 wt. %, less than about 13 wt. %, less than about 12 wt. %, less than about 11 wt. %, less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, or less than about lwt. % of the total weight of active agent present in the composition, is released along with the placebo layer.

In certain embodiments, less that about 20 wt. %, less than about 15 wt. %, less than about 10 wt. %, less than about 5 wt. %, less than about 4 wt. %, less than about 3 wt. %, less than about 2 wt. %, or less than about 1 wt. % of active agent, based on the total weight of active agent present in the composition, is released between about 2 hours and about 8 hours, between about 2 hours and about 7 hours, or between about 2 hours and about 6 hours following administration of the dosage form, thereby providing a lag time.

Placebo Layer/Placebo Layer Blend

In certain embodiments, the placebo layer/placebo layer blend, is located adjacent to and in continuity with the orifice in the semipermeable membrane. In certain embodiments, the placebo layer comprises at least one swellable hydrophilic polymer, a binder, a stabilizer, a color pigment, and a glidant. In certain embodiments, the placebo layer further comprises an osmogen and/or a wicking agent. In certain embodiments, presence of color pigment and/or stabilizers is optional. In certain embodiments, presence of osmogen and/or wicking agent is optional. In certain embodiments, the placebo layer comprises placebo layer granules and extragranular components. In certain embodiments, placebo layer granules comprise at least one swellable hydrophilic polymer, a binder, a stabilizer, and a color pigment. In certain embodiments, placebo layer granules further comprise an osmogen and/or a wicking agent. In certain embodiments, presence of color pigment and/or stabilizers in the granules is optional. In certain embodiments, presence of wicking agent and/or osmogen in the granules is optional. In certain embodiments, extragranular components comprise glidants and lubricants. In certain embodiments, the placebo layer blend comprises a swellable hydrophilic polymer, e.g., polyethylene oxide polymer with an average molecular weight of from about 300,000 Da to about 900,000 Da, e.g., from about 400,000 Da to about 900,000 Da, a binder, a lubricant, and a glidant. In certain embodiments, the placebo layer/placebo layer blend is substantially free of active agent, e.g., armodafinil, modafinil, or pharmaceutically acceptable salts thereof. In certain embodiments, the placebo layer contains less than about 30 wt. %, less than about 25 wt. %, less than about 20 wt. %, less than about 15 wt. %, less than about 10 wt. %, less than 9 wt. %, less than 8 wt. %, less than 7 wt. %, less than 6 wt. %, less than about 5 wt. %, less than 4 wt. %, less than 3 wt. %, less than 2 wt. %, less than 1 wt. %, or any intermediate values therein, of armodafinil, modafinil, or pharmaceutically acceptable salts thereof, based on the total weight of the armodafinil, modafinil, or a pharmaceutically acceptable salt thereof, present in the core.

In certain embodiments, the placebo layer includes a stabilizer to prevent degradation of polyethylene oxide polymer, e.g., POLYOX®. In certain embodiments, the placebo layer includes at least one osmogen and/or at least one wicking agent. In certain embodiments, the presence of osmogen and/or wicking agent is optional. In certain embodiments, placebo layer includes granules and extragranular excipients. In certain embodiments, the granules comprise a swellable hydrophilic polymer, a binder, an osmogen, a stabilizer, and a color pigment. In certain embodiments, granules further include a wicking agent. In certain embodiments, glidant and lubricant are present as extragranular excipients in the placebo layer. In certain embodiments, the granulating solvent for making granules comprises an alcoholic solvent. In certain embodiments, the granulation solvent comprises a hydroalcoholic solvent comprising alcohol and deionized water in varying weight ratios. In certain embodiments, the granulation solvent is a hydroalcoholic solvent containing alcohol:water weight ratio of between about 50:50 and about 99:1. In certain embodiments, the alcoholic solvent comprises dehydrated alcohol/absolute alcohol, and/or isopropyl alcohol. In certain embodiments, the placebo layer blend is made by dry granulation/slugging. In certain embodiments, the placebo layer is made by direct compaction In certain embodiments, the molecular weight/grade of the polyethylene oxide polymer in the placebo layer affects drug recovery, lag time, and/or release profile, of the composition. In certain embodiments, the polyethylene oxide polymer has an average molecular weight of less than about 1,000,000 Da, e.g., about 400,000 Da (e.g., sold under the trademark POLYOX®WSR 301), about 600,000 Da (e.g., sold under the trademark POLYOX®WSR 205), about 900,000 Da (e.g., sold under the trademark POLYOX® WSR 1105), or intermediate weights therein.

In certain embodiments, the viscosity of the placebo layer in aqueous medium can be adjusted to provide a desired and consistent lag time. In certain embodiments, the viscosity of the placebo layer in aqueous medium depends upon the average molecular weight of the polyethylene oxide polymer present in the placebo layer. In certain embodiments, the placebo layer contains a polyethylene oxide polymer with an average molecular weight of about 400,000 Da that is sold under the trademark POLYOX® WSR 301, a polyethylene oxide polymer with an average molecular weight of about 600,000 Da that is sold under the trademark POLYOX®WSR 205, or a polyethylene oxide polymer with an average molecular weight of about 900,000 Da that is sold under the trademark POLYOX® WSR 1105. In certain embodiments, the placebo layer contains a polyethylene oxide polymer with an average molecular weight of about 900,000 Da that is sold under the trademark POLYOX® WSR 1105. In certain embodiments, the placebo layer contains a polyethylene oxide polymer with an average molecular weight of about 600,000 Da that is sold under the trademark POLYOX® WSR 205. In certain embodiments, the polyethylene oxide polymer is present in an amount of from about 40 wt. % to about 99 wt. %, based on the total weight of the placebo layer. In certain embodiments, the polyethylene oxide polymer is present in an amount of about 40 wt. %, about 45 wt. %, about 50 wt. %, about 51 wt. %, wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, about 95 wt. %, about 96 wt. %, about 97 wt. %, about 98 wt. %, about 99 wt. %, or any intermediate values therein, based on the total weight of the placebo layer.

In certain embodiments, the placebo layer comprises binders comprising, but not limited to, povidone, hypromellose, starch, acacia, gellan gum, hydroxypropyl cellulose, methylcellulose, sodium carboxymethylcellulose, polyvinyl alcohol, polyvinyl acetates, polyethylene oxide, polyethylene glycol, alginates, pegylated polyvinyl alcohol, or any combination thereof. In certain embodiments, the binder is povidone. In certain embodiments, the binders are present in an amount of about 0.5 wt. % to about 50 wt. % of the placebo layer. In certain embodiments, the binders are present in an amount of about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, or any intermediates values therein, based on the total weight of the placebo layer.

In certain embodiments, the placebo layer includes at least one stabilizer to prevent/slow the degradation of the polyethylene oxide polymer. In certain embodiments, the stabilizer comprises antioxidants including ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the antioxidant is BHT. In certain embodiments, the stabilizer is present in an amount of about 0.01 wt. % to about 0.5 wt. % of the placebo layer. In certain embodiments, the stabilizer is present in an amount of about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.10 wt. %, about 0.2 wt. %, about 0.3 wt. %, about 0.4 wt. %, about 0.5 wt. %, or any intermediate values therein, based on the total weight of the placebo layer.

In certain embodiments, the placebo layer comprises at least one lubricant comprising, but not limited to, magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combination thereof. In certain embodiments, the lubricant is magnesium stearate or steric acid. In certain embodiments, the placebo layer comprises at least one lubricant as an extragranular excipient. In certain embodiments, the lubricant is present in an amount of about 0.1 wt. % to about 10 wt. %, based on the total weight of the placebo layer.

In certain embodiments, the lubricant is present in an amount of about 0.1 Wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, or any intermediate values therein, based on the total weight of the placebo layer.

In certain embodiments, the placebo layer comprises at least one glidant, comprising, but not limited to, talc, colloidal silicon dioxide, magnesium trisilicate, powdered cellulose, starch, tribasic calcium phosphate, or any combinations thereof. In certain embodiments, the glidant is colloidal silicon dioxide. In certain embodiments, the placebo layer comprises at least one glidant as an extragranular excipient. In certain embodiments, the glidant is present in an amount of from about 0.05 wt. % to about 10 wt. %, from about 0.1 wt. % to about 5 wt. %, from about 0.5 wt. % to about 5 wt. %, from about 1 wt. % to about 5 wt. %, from about 1.5 wt. % to about 5 wt. %, from about 2 wt. % to about 5 wt. %, from about 2.5 wt. % to about 5 wt. %, from about 3 wt. % to about 5 wt. %, from about 3.5 wt. % to about 5 wt. %, from about 4 wt. % to about 5 wt. %, from about 4.5 wt. % to about 5 wt. %, from about 0.05 wt. % to about 4.5 wt. %, from about 0.05 wt. % to about 4.0 wt. %, from about 0.05 wt. % to about 3.5 wt. %, from about 0.05 wt. % to about 3.0 wt. %, from about 0.05 wt. % to about 2.5 wt. %, from about 0.05 wt. % to about 2.0 wt. %, from about 0.05 wt. % to about 1.5 wt. %, from about 0.05 wt. % to about 1.0 wt. %, from about 0.05 wt. % to about 0.5 wt. %, from about 0.05 wt. % to about 0.1 wt. %, from about 0.1 wt. % to about 4.5 wt %, from about 1 wt. % to about 4 wt. %, or from about 1.5 wt. % to about 3 wt. %, based on the total weight of the placebo layer. In certain embodiments, the glidant is present in an amount of about 0.05 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, or any intermediate valued therein, based on the total weight of the placebo layer.

In certain embodiments, the placebo layer includes at least one color pigment. In certain embodiments, the color pigment in the placebo layer is useful for distinguishing the placebo layer from the active layer. In certain embodiments, the color pigment comprises iron oxide or lake-based colors. In certain embodiments, the pigment is a lake-based color. In certain embodiments, the pigment is an iron oxide pigment, e.g., oxide pigment red or oxide pigment black. In certain embodiments, the pigment is present in an amount of about 0.01 wt. % to about 5 wt. %, based on the total weight of the placebo layer.

In certain embodiments, the placebo layer further comprises osmogens, and/or disintegrants or water-entraining agents/wicking agents.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of from about 0 wt. % to about 60 wt. %, based on the total weight of the placebo layer. In certain embodiments, the osmogen is present in an amount of about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, or any intermediate values therein, based on the total weight of the placebo layer.

In certain embodiments, the placebo layer comprises at least one wicking agent selected from the group comprising crospovidone, croscarmellose sodium, carmellose calcium, polyvinyl pyrrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 0 wt. % to about 40 wt. %, based on the total weight of the placebo layer. In certain embodiments, the wicking agent is present in an amount of 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, or any intermediate values therein, based on the total weight of the placebo layer.

In certain embodiments, the relative weight percentage of the placebo layer, based on the total weight of the uncoated trilayer core, can be from about 10 wt. % to about 40 wt. %.

Active Layer/Active Layer Blend

In certain embodiments, the active layer/active layer blend is located between (and adjacent to) and in contact with the placebo layer and the push layer. In certain embodiments, the active layer/active layer blend includes armodafinil/modafinil or pharmaceutically acceptable salts thereof, at least one swellable hydrophilic polymer, a binder, and a lubricant. In certain embodiments, the active layer/active layer blend further includes a surfactant, an osmogen, a wicking agent, a glidant and/or a stabilizer. In certain embodiments, active layer blend includes active layer granules comprising armodafinil, modafinil, or pharmaceutically acceptable salts thereof, a swellable hydrophilic polymer, a binder, an osmogen, a stabilizer, and a color pigment. In certain embodiments, granules further include a surfactant and/or a wicking agent. In certain embodiments, the presence of osmogen, wicking agent, surfactant, and/or stabilizer is optional. In certain embodiments, the glidants and the lubricants are present as extragranular excipients in the active layer blend.

In certain embodiments, the granulating solvent for making granules comprises an alcoholic solvent. In certain embodiments, the granulation solvent comprises a hydroalcoholic solvent comprising alcohol and deionized water in varying weight ratios. In certain embodiments, the granulation solvent is a hydroalcoholic solvent containing alcohol: water weight ratio of between about 50:50 and about 99:1. In certain embodiments, the alcoholic solvent comprises dehydrated alcohol/absolute alcohol, and/or isopropyl alcohol. In certain embodiments, the active layer blend is made by dry granulation/slugging. In certain embodiments, the active layer is made by direct compaction. In certain embodiments, the swellable hydrophilic polymers comprise polyethylene oxide, carbopols, polyacrylamides, acrylate polymer polysaccharide composed of condensed glucose units, crospovidone, carboxymethyl cellulose, and poly(alkalicarboxymethylcellulose), METHOCEL™ K100LVCR (methylcellulose and hydroxypropyl methyl cellulose), and any combinations thereof. In certain embodiments, the swellable hydrophilic polymers comprise polyethylene oxide polymers with an average molecular weight of from about 100,000 Da to about 300,000 Da. In certain embodiments, the polyethylene oxide polymer has an average molecular weight of about 100,000 Da (e.g., polyethylene oxide polymer sold under the trademark POLYOX® WSR N-10), about 200,000 Da (e.g., polyethylene oxide polymer sold under the trademark POLYOX® N-80), or about 300,000 Da (e.g., polyethylene oxide polymer sold under the trademark POLYOX®WSR N-750), or any intermediate weights therein. In certain embodiments, the average molecular weight of the polyethylene oxide polymer is about 200,000 Da.

In certain embodiments, viscosity in aqueous medium of the active layer is adjusted to provide a desired and consistent release profile. In certain embodiments, the viscosity in aqueous medium of active layer depends upon the average molecular weight/grade of the the polyethylene oxide polymer present in the active layer. In certain embodiments, the active layer contains a polyethylene oxide polymer with an average molecular weight of about 200,000 Da. In certain embodiments, the active layer contains a polyethylene oxide polymer with an average molecular weight of about 300,000 Da. In certain embodiments, the polyethylene oxide polymer is present in an amount of from about 5 wt. % to about 50 wt. % of the active layer. In certain embodiments, the polyethylene oxide polymer is present in an amount of about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 45 wt. %, about 50 wt. %, or intermediate values therein, based on the total weight of the active layer.

In certain embodiments, drug to polyethylene oxide polymer weight ratio, in the active layer, affects the lag time, release rate, and drug recovery of the composition. In certain embodiments, release rate and drug recovery from the composition increases with increasing the drug to polyethylene oxide polymer weight ratio. In certain embodiments, lag time decreases with increasing drug to polyethylene oxide polymer weight ratio. In certain embodiments, the ratio of the armodafinil/modafinil or pharmaceutically acceptable salts thereof and polyethylene oxide polymer is between about 40:60 and about 95:5. In certain embodiments, the weight ratio of the drug and the polyethylene oxide polymer is about 40:60, about 45:55, about 50:50, about 55:45, about 60:40, about 65:35, about 70:30, about 75:25, about 80:20, about 85:15, about 90:10, about 95:5, or intermediate ratios therein. In certain embodiments, the armodafinil/modafinil or pharmaceutically acceptable salts: polyethylene oxide polymer weight ratio is from about 50:50 and about 90:10.

In certain embodiments, the active layer comprises binders including povidone, hypromellose, starch, acacia, gellan gum, hydroxypropyl cellulose, methylcellulose, sodium methylcellulose, polyvinyl alcohol, polyvinyl acetates, polyethylene oxide, polyethylene glycol, alginates, pegylated polyvinyl alcohol, or any combination thereof. In certain embodiments, the binder is povidone. In certain embodiments, the binders are present in an amount of about 0.5 wt. % to about 50 wt. %, 0.5 wt. % to about 29 wt. %, from about 0.5 wt. % to about 28 wt. %, from about 0.5 wt. % to about 27 wt. %, from about 0.5 wt. % to about 26 wt. %, from about 0.5 wt. % to about 25 wt. %, from about 0.5 wt. % to about 24 wt. %, from about 0.5 wt. % to about 23 wt. %, from about 0.5 wt. % to about 22 wt. %, from about 0.5 wt. % to about 21 wt. %, from about 0.5 wt. % to about 20 wt. %, from about 0.5 wt. % to about 19 wt. %, from about 0.5 wt. % to about 18 wt. %, from about 0.5 wt. % to about 17 wt. %, from about 0.5 wt. % to about 16 wt. %, from about 0.5 wt. % to about 15 wt. %, from about 0.5 wt. % to about 14 wt. %, from about 0.5 wt. % to about 13 wt. %, from about 0.5 wt. % to about 12 wt. %, from about 0.5 wt. % to about 11 wt. %, from about 0.5 wt. % to about 10 wt. %, from about 0.5 wt. % to about 9 wt. %, from about 0.5 wt. % to about 8 wt. %, from about 0.5 wt. % to about 7 wt. %, from about 0.5 wt. % to about 6 wt. %, from about 0.5 wt. % to about 5 wt. %, from about 0.5 wt. % to about 4 wt. %, from about 0.5 wt. % to about 3 wt. %, from about 0.5 wt. % to about 2 wt. %, from about 0.5 wt. % to about 1 wt %, from about 1 wt. % to about 20 wt. %, from about 2 wt. %, to about 20 wt. %, from about 3 wt. % to about 20 wt. %, from about 4 wt. % to about 20 wt. %, from about 5 wt. % to about 20 wt. %, from about 6 wt. % to about 20 wt. %, from about 7 wt. % to about 20 wt. %, from about 8 wt. % to about 20 wt. %, from about 9 wt. % to about 20 wt. %, from about 10 wt. % to about 20 wt. %, from about 11 wt. % to about 20 wt. %, from about 12 wt. % to about 20 wt. %, from about 13 wt. % to about 20 wt. %, from about 14 wt. % to about 20 wt. %, from about 15 wt. % to about 20 wt. %, from about 16 wt. % to about 20 wt. %, from about 17 wt. % to about 20 wt. %, from about 18 wt. % to about 20 wt. %, from about 19 wt. % to about 20 wt. %, from about 5 wt. % to about 15 wt. %, from about 5 wt. % to about 10 wt. %, or from about 10 wt. % to about 15 wt. %, based on the total weight of the active layer.

In certain embodiments, the active layer comprises osmogens and/or any wicking agents. In certain embodiments, the active layer comprises at least one osmogen. In certain embodiments, the osmogen includes ionic compounds of inorganic salts that provide a concentration differential for osmotic flow of liquid into the composition. In certain embodiments, the osmogen comprises an ionic compound including sodium chloride, potassium chloride, potassium sulfate, lithium sulfate, sodium sulfate, a lactose and sucrose combination, a lactose and dextrose combination, sucrose, dextrose, mannitol, dibasic sodium phosphate, and any combination thereof. In certain embodiments, the osmogen is sodium chloride. In certain embodiments, the osmogen is present in an amount of from about 0 wt. % to about 60 wt. %, based on the total weight of the active layer. In certain embodiments, the osmogen is present in an amount of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, or any intermediate values therein, based on the total weight of the active layer.

In certain embodiments, the active layer comprises at least one wicking agent selected from the group comprising crospovidone, croscarmellose sodium, carmellose calcium, polyvinyl pyrrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 0 wt. % to about 40 wt. %, based on the total weight of the active layer. In certain embodiments, the wicking agent is present in an amount of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, or any intermediate values therein, based on the total weight of the active layer.

In certain embodiments, the active layer includes at least one stabilizer to prevent/reduce the degradation of the polyethylene oxide polymer present in the active layer. In certain embodiments, the stabilizer comprises an antioxidant and/or a pH modifying agent. In certain embodiments, the pH modifying agent is an acid or a base. In certain embodiments, the stabilizer is an antioxidant and a pH modifying agent. In certain embodiments, the stabilizer comprises an antioxidant including one or more of ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, and propyl gallate. In certain embodiments, the antioxidant is BHT. In certain embodiments, additional stabilizers, e.g., pH modifiers, can be added to stabilize the active agent. In certain embodiments, the stabilizer is present in an amount of about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.10 wt. %, about 0.2 wt. %, about 0.3 wt. %, about 0.4 wt. %, about 0.5 wt. %, or any intermediate values therein, based on the total weight of the active layer.

In certain embodiments, the compositions of the disclosure release active agents, e.g., armodafinil, modafinil, or pharmaceutically acceptable salts thereof, in lower portions of the GI tract with minimal amounts of fluid, e.g., colon. In certain embodiments, such release of the active agent in areas of the GI tract with minimal amount of fluid reduces their solubility. In certain embodiments, the active layer comprises surfactants to modulate the solubility of active agents. In certain embodiments, the surfactant is added to improve solubility of active agents in lower GI tract, e.g., portions of the GI tract containing minimal amount of fluid, e.g., colon. In certain embodiments, the surfactant comprises one or more of esters of fatty acids; sorbitan fatty acid esters ethoxylated with from about 2 to about 30 moles of ethylene oxide; polyethylene glycol fatty acid esters; polyethylene glycol esters and polyethylene glycol ethers; and polyethoxylated carboxylic acids, PEG-7 hydrogenated castor oil (polyethylene glycol derivative of hydrogenated castor oil with average of 7 moles of ethylene oxide), and PEG-30 dipolyhydroxystearate polyethylene glycol diester of polyhydroxy stearic acid); block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; polyoxyl 40 stearate, and any mixtures thereof. In certain embodiments, the surfactants are present in an amount of from about 0 wt. % to about 10 wt. %, based on the total weight of the active layer. In certain embodiments, the surfactants are present in an amount of from about 0.5 wt. %, about 1 wt. %, about 1.5 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.5 wt. %, about 5 wt. %, about 5.5 wt. %, about 6 wt. %, about 6.5 wt. %, about 7 wt. %, about 7.5 wt. %, about 8 wt. %, about 8.5 wt. %, about 9 wt. %, about 9.5 wt. %, about 10 wt. %, or any intermediate values therein, based on the total weight of the active layer.

In certain embodiments, the active layer comprises lubricants including magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, or any combination thereof. In certain embodiments, the lubricant is present in an amount of about 0.5 wt. % to about 5 wt. %, based on the total weight of the active layer. In certain embodiments, the lubricant is present in an amount of about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, or any intermediate values therein, based on the total weight of the active layer.

In certain embodiments, the active layer comprises glidants including talc, colloidal silicon dioxide, magnesium trisilicate, powdered cellulose, starch, tribasic calcium phosphate, or a mixture thereof. In certain embodiments, the glidant is colloidal silicon dioxide. In certain embodiments, the glidant is present in an amount of about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, or any intermediate values therein, based on the total weight of the active layer.

In certain embodiments, the relative weight percentage of the active layer, based on the total weight of the uncoated trilayer core, can be between about 20 wt. % and about 70 wt. %.

Push Layer/Push Layer Blend

In certain embodiments, the push layer/push layer blend is located adjacent to the active layer. In certain embodiments, the push layer/push layer blend includes at least one swellable hydrophilic polymer, a binder, an osmogen, a lubricant, a glidant, and a color pigment. In certain embodiments, the push layer further includes a stabilizer. In certain embodiments, the push layer blend includes granules comprising a swellable hydrophilic polymer, a binder, an osmogen, a stabilizer, and a color pigment. In certain embodiments, the glidants and the lubricants are present as extragranular excipients in the push layer blend. In certain embodiments, the granulating solvent for making granules comprises an alcoholic solvent. In certain embodiments, the granulation solvent comprises a hydroalcoholic solvent comprising alcohol and deionized water in varying weight ratios. In certain embodiments, the granulation solvent is a hydroalcoholic solvent containing alcohol:water weight ratio of between about 50:50 and about 99:1. In certain embodiments, the alcoholic solvent comprises dehydrated alcohol/absolute alcohol, and/or isopropyl alcohol. In certain embodiments, the push layer blend is made by dry granulation/slugging. In certain embodiments, the push layer is made by direct compaction.

In certain embodiments, the push layer does not include any active agent/drug. In certain embodiments, the swellable hydrophilic polymer is a polyethylene oxide polymer having an average molecular weight of greater than or equal to 1000,000 Da.

In certain embodiments, the average molecular weight of the polyethylene oxide polymer in the push layer is about 1000,000 Da (e.g., polyethylene oxide polymer sold under the trademark POLYOX® WSR N 12K), about 2000,000 Da (e.g., polyethylene oxide polymer sold under the trademark POLYOX® WSR N 60K), about 4000,000 Da (e.g., polyethylene oxide polymer sold under the trademark POLYOX® WSR 301), about 5000,000 Da (e.g., polyethylene oxide polymer sold under the trademark POLYOX® WSR coagulant), about 7000,000 Da (e.g., polyethylene oxide polymer sold under the trademark POLYOX® WSR 303), or any intermediate values therein. In certain embodiments, swelling of polyethylene oxide polymer sold under the trademark POLYOX® WSR coagulant can be enhanced by mixing with a portion of polyethylene oxide polymer sold under the trademark POLYOX® WSR 303. In certain embodiments, swelling of polyethylene oxide polymer sold under the trademark POLYOX® WSR coagulant can be reduced by mixing with a portion of the polyethylene oxide polymer sold under the trademark POLYOX® WSR 301. In certain embodiments, the polyethylene oxide polymer is present in an amount of about 40 wt. % to about 90 wt. %, from about 40 wt. % to about 80 wt. %, from about 40 wt. % to about 75 wt. %, from about 40 wt. % to about 70 wt. %, from about 40 wt. % to about 65 wt. %, from about 40 wt. % to 60 wt. %, from about 40 wt. % to 55 wt. %, from about 40 wt. % to 50 wt. %, from about 40 wt. % to 45 wt. %, from about 45 wt. % to about 80 wt. %, from about 50 wt. % to about 80 wt. %, from about 55 wt. % to about 80 wt. %, from about 60 wt. % to about 80 wt. %, from about 65 wt. % to about 80 wt. %, from about 70 wt. % to about 80 wt. %, from about 75 wt. % to about 80 wt. %, from about 45 wt. % to about 75 wt. %, from about 50 wt. % to about 70 wt. %, or from about 55 wt. % to about 65 wt. %, based on the total weight of the push layer. In certain embodiments, the polyethylene oxide polymer is present in an amount of about 45 wt. %, about 50 wt. %, about 55 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, or any intermediate values therein, based on the total weight of the push layer.

In certain embodiments, the amount and grade of the polyethylene oxide polymer present in the push layer affects the release profile of the drug from the dosage form, i.e., an increase in the molecular weight or amount of the polyethylene oxide polymer in the push layer will increase the force exerted on the pull layer for fast and complete drug recovery. In certain embodiments, the grade of the polyethylene oxide polymer in the push layer is selected to provide desired lag time, release rate, and complete drug recovery in about 22 hours from the time of administration of the dosage form.

In certain embodiments, the push layer comprises at least one osmogen. In certain embodiments, the presence of osmogen in the push layer is essential for uniform swelling of the composition core. In certain embodiments, the osmogen provides a concentration gradient for osmotic flow of liquid into the composition. Amount of liquid available for absorption by the polyethylene oxide polymer present in the push layer depends upon the imbibition rate of the liquid. In certain embodiments, imbibition rate depends upon osmotic pressure generated by the osmogen present in the composition (e.g., push layer), and the permeability of the semipermeable membrane/functional coat. As the polyethylene oxide polymer present in the push layer absorbs the imbibed liquid, it expands in volume, which pushes the drug solution or suspension in the pull layer out of the tablet through the orifice/hole in the membrane. The compositions release drug at a rate, which is independent of pH and hydrodynamics of the dissolution medium.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of about 5 wt. % to about 60 wt. %, based on the total weight of the push layer. In certain embodiments, the osmogen is present in an amount of about 10 wt. % to about 60 wt. %, based on the total weight of the push layer. In certain embodiments, the osmogen is present in an amount of about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 50 wt. %, about 55 wt. %, about 60 wt. %, or any intermediate values therein, based on the total weight of the push layer. In certain embodiments, the osmogen is present in an amount of from about 10 wt. % to about 30 wt. %, based on the total weight of the push layer.

In certain embodiments, the push layer includes at least one binder selected from the group consisting of, but not limited to, povidone, hypromellose, starch, acacia, gellan gum, low viscosity hydroxypropyl cellulose, methylcellulose, sodium methylcellulose, polyvinyl alcohol, polyvinyl acetates, polyethylene oxide, polyethylene glycol, alginates, pegylated polyvinyl alcohol, and any combination thereof. In certain embodiments, the binder is povidone. In certain embodiments, the binders are present in an amount of about 0.05 wt. % to about 50 wt, based on the total weight of the push layer. In certain embodiments, the binders are present in an amount of about 0.05 wt. %, about 0.1 wt. %, about 0.2 wt. %, about 0.2 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 10 wt. %, about 15 wt. %, about 20 wt. %, or any intermediates values therein, based on the total weight of the push layer.

In certain embodiments, the push layer includes at least one stabilizer to prevent/reduce degradation of POLYOX®. In certain embodiments, the stabilizer comprises, but is not limited to, ascorbic acid, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the stabilizer is BHT. In certain embodiments, the stabilizer is present in an amount of about 0.05 wt. % to about 15 wt. %, based on the total weight of the push layer. In certain embodiments, the stabilizer is present in an amount of about 0.05 wt. %, about 0.1 wt. %, about 0.15 wt. %, about 0.5 wt. %, 1 wt. %, about 1.5 wt. %, about 2 wt. %, about 2.5 wt. %, about 3 wt. %, about 3.5 wt. %, about 4 wt. %, about 4.5 wt. %, about 5 wt. %, about 5.5 wt. %, about 6 wt. %, about 6.5 wt. %, about 7 wt. %, about 7.5 wt. %, about 8 wt. %, about 8.5 wt. %, about 9 wt. %, about 9.5 wt. %, about 10 wt. %, about 10.5 wt. %, about 11 wt. %, about 11.5 wt. %, about 12 wt. %, about 12.5 wt. %, about 13 wt. %, about 13.5 wt. %, about 14 wt. %, about 14.5 wt. %, about 15 wt. %, or any intermediate values therein, based on the total weight of the push layer.

In certain embodiments, the push layer includes lubricants comprising, but not limited to, magnesium stearate, glyceryl monostearates, palmitic acid, talc, carnauba wax, calcium stearate sodium, sodium or magnesium lauryl sulfate, calcium soaps, zinc stearate, polyethylene oxide, polyethylene glycols, polyoxyethylene monostearates, calcium silicate, silicon dioxide, hydrogenated vegetable oils and fats, stearic acid, or any combination thereof. In certain embodiments, the lubricant is present in an amount of about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, or any intermediate values therein, based on the total weight of the push layer.

In certain embodiments, the push layer includes at least one glidant comprising, but not limited to, talc, colloidal silicon dioxide, magnesium trisilicate, powdered cellulose, starch, and tribasic calcium phosphate. In certain embodiments, the glidant is colloidal silicon dioxide. In certain embodiments, the glidant is present in an amount of about 0.1 wt. %, about 0.2 wt. %, about 0.3 wt. %, about 0.4 wt.

%, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, or any intermediate valued therein, based on the total weight of the push layer.

In certain embodiments, the push layer includes at least one color pigment for identifying the push layer in the multilayer tablet core. In certain embodiments, the push layer and the placebo layer include the same color pigment. In certain embodiments, the placebo layer contains less amount of color pigment than the push layer. In certain embodiments, the push layer is darker in color than the placebo layer, which helps in identifying the placebo layer side while drilling a orifice in the membrane on the placebo layer side of the multilayer core. In certain embodiments, the push layer includes at least one pigment comprising iron oxide or lake-based colors. In certain embodiments, the pigment is a lake-based color. In certain embodiments, the pigment is an iron oxide pigment, e.g., oxide pigment red, and oxide pigment black. In certain embodiments, the pigment is present in an amount of about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, or any intermediate values therein, based on the total weight of the push layer.

In certain embodiments, the weight of the push layer is from about 10 wt. % to about 40 wt. %, based on the total weight of the trilayer core.

Semipermeable Membrane/Functional Coat

In certain embodiments, the trilayer tablet core is coated with a semipermeable membrane. In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the orifice into the core, and not too small to build hydrostatic pressure within the core.

In certain embodiments, the orifice is made via manual or laser drilling. In certain embodiments, the optimum orifice diameter is less than about 2.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

In certain embodiments, the coating composition and/or coating weight gain of the semipermeable membrane determines the lag time provided by the composition. In certain embodiments, the coating weight gain of the semipermeable membrane ranges from about 1 wt. % to about 30 wt. %, based on the total weight of the uncoated tablet core. In certain embodiments, the coating weight gain of the semipermeable membrane ranges from about 1 wt. % to about 20 wt. %, based on the total weight of the uncoated tablet core. In certain embodiments, the coating weight gain is about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, or any intermediate values therein, based on the total weight of the uncoated tablet core.

In certain embodiments, the semipermeable membrane coat over the multilayered tablet core is substantially impermeable to drugs and excipients present in the composition. In certain embodiments, the semipermeable membrane is permeable to solvents/dissolution medium, e.g., water, GI fluid, and simulated GI fluid. In certain embodiments, the semipermeable membrane doesn't react with gastric fluid regardless of the pH. In certain embodiments, the semipermeable membrane maintains the integrity of the composition to provide constant osmotic pressure during drug delivery. In certain embodiments, the semipermeable membrane comprises one or more water-insoluble polymers that are permeable to water and substantially impermeable to solutes, e.g., drugs and excipients. In certain embodiments, the water-insoluble polymers are pH independent polymers. Polymers suitable for inclusion in the semipermeable membrane comprise cellulose esters, e.g., cellulose acetate, cellulose diacetate, cellulose triacetate, cellulose propionate, cellulose acetate butyrate, and combinations thereof. In certain embodiments, the semipermeable membrane comprises cellulose acetate. In certain embodiments, the permeability of the semipermeable membrane can be enhanced by increasing the acetyl content in cellulose acetate. In certain embodiments, the semipermeable membrane comprises cellulose acetate with at least about 30% acetyl content. In certain embodiments, the semipermeable membrane comprises cellulose acetate with about 32% acetyl content, about 35% acetyl content, about 38% acetyl content, about 39% acetyl content, or about 39.8% acetyl content. In certain embodiments, permeability of the semipermeable membrane is enhanced by addition of water-soluble pore formers to the membrane composition. In certain embodiments, the pore formers are pH-independent water-soluble pore formers. In certain embodiments, the water-soluble pore formers comprise, but are not limited to, of polyethylene glycol (PEG 400, PEG 1000, PEG 1450, PEG 3350), hydroxypropyl cellulose, polyvinyl pyrrolidone (sold under the trademark KOLLIDON® 30), polyvinyl alcohol/polyethylene glycol graft copolymer (sold under the trademark KOLLICOAT® IR), sucrose, glucose, fructose, lactose, mannose, mannitol, sorbitol, methyl cellulose (sold under the trademark METHOCEL™ E3, METHOCEL™ E5, METHOCEL™ E6), poloxamers, e.g., poloxamer 188, triethyl citrate, triacetin, hydroxypropyl methylcellulose, polyhydric alcohols such as glycerol, and combinations thereof. In certain embodiments, the semipermeable membrane comprises cellulose acetate and a pore former comprising polyethylene glycol. In certain embodiments, the water-insoluble polymer is cellulose acetate and the pore former is polyethylene glycol 3350. In certain embodiments, weight ratio of water-insoluble polymer to pore former is between about 70:30 and about 99.5:0.5. In certain embodiments, weight ratio of water-insoluble polymer to pore former is between about 80:20 and about 99.5:0.5. In certain embodiments, weight ratio of cellulose acetate to polyethylene glycol is between about 80:20 and about 99.5:0.5. In certain embodiments, the ratio of cellulose acetate to poloxamer is between about 80:20 and about 99.5:0.5. In certain embodiments, weight ratio of cellulose acetate and pore former affects variability in lag time. In certain embodiments, variability in lag time decreases with increasing the amount of pore former in the membrane. In certain embodiments, lag time decreases with increasing the amount of pore former in the membrane. In certain embodiments, the weight ratio of cellulose acetate and pore former is optimized to obtain a desired lag time with minimal variability. In certain embodiments, the weight ratio of cellulose acetate and pore former is about 80:20, about 85:15, about 90:10, about 95:5, about 96:4, about 97:3, about 98:2, about 99:1, about 99.5:0.5, or any intermediate values therein.

In certain embodiments, the semipermeable membranes include one or more plasticizers. Plasticizers play a significant role in adjusting flexibility and permeability of the semipermeable membrane. Plasticizers change the viscoelastic behavior and permeability of the polymer present in the semipermeable membrane. Plasticizers can convert a hard and brittle polymer into a softer and more pliable material that has more mechanical strength. Plasticizers used in the semipermeable membranes comprise polyethylene glycols, triethyl citrate, triacetin, diethyl tartrate, dibutyl sebacate, and combinations thereof. In certain embodiments, coating solvents used for coating comprise, but are not limited to, methylene chloride, carbon tetra chloride, acetone, methanol, ethanol, water, and/or any mixtures thereof. In certain embodiments, the coating solvent is a mixture of acetone and water. In certain embodiments, the acetone:water weight ratio is between 70:30 and 95:5. In certain embodiments, the acetone:water weight ratio is about 80:20, about 85:15, about 90:10, about 95:5, or any intermediate values therein.

In certain embodiments, the oral compositions of the disclosure include an aesthetic coat over the semipermeable membrane. In certain embodiments, the aesthetic coat comprises colors, flavors, and sweeteners. In certain embodiments, the aesthetic coat is the outermost coat comprising a mixture of polyvinyl alcohol, talc, polyethylene glycol, and polysorbate 80 (sold under the trademark OPADRY® II) for pigmentation or a mixture of maltodextrin, talc, hypromellose, guar gum, and medium chain triglycerides (sold under the trademark OPADRY® clear) for final glossiness. In certain embodiments, the aesthetic coat further comprises wax to improve flow for packaging.

6.3. Embodiments of the Dosage Form

A nonlimiting set of exemplary osmotic-controlled compositions follows.

In certain embodiments, the compositions of the disclosure provide delayed release of armodafinil/modafinil or pharmaceutically acceptable salts thereof. In certain embodiments, the compositions of the disclosure comprise a multilayer tablet core coated with a semipermeable membrane containing at least one orifice. The multilayered tablet core comprises a pull layer containing the active agent, and a push layer. The pull layer comprises at least two layers: a placebo layer, for providing a desired lag time for the release of the active agent; and an active layer containing the active agent and providing a delayed release of the active agent. In certain embodiments, the active agent is armodafinil or a pharmaceutically acceptable salt thereof. In certain embodiments, the active agent is modafinil or a pharmaceutically acceptable salt thereof.

In certain embodiments, the tablet core comprises multiple layers in the following order: a placebo layer facing the at least one orifice present in the semipermeable membrane, an active layer containing armodafinil/modafinil or pharmaceutically acceptable salts thereof for delayed release, and a push layer, wherein the push layer is away (e.g., furthest away) from the orifice in the semipermeable membrane. In certain embodiments, each of the push layer, the placebo layer, and the active layer, exhibit a viscosity, measured using Brookfield viscometer, in 1% aqueous solution at 25° C., wherein the viscosity of the push layer >viscosity of the placebo layer >viscosity of the active layer. In certain embodiments, the number of orifices in the semipermeable membrane can be one, two, three, or four. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or any intermediate values therein. In certain embodiments, the semipermeable membrane facing the top of the placebo layer is completely removed to provide an orifice comprising an optimum diameter that is equivalent to the diameter of the top of the placebo layer end of the multilayer core.

In certain embodiments, the disclosure provides methods for manufacturing delayed release armodafinil/modafinil compositions comprising a multilayer core comprising a pull layer and a push layer; and a semipermeable membrane over the multilayer core. The semipermeable membrane comprises at least one orifice and covers at least a portion of the multilayer core. The pull layer comprises a placebo layer and an active layer. The pull layer and the push layer in the multilayer compositions of the disclosure comprise granules made by wet granulation. In certain embodiments, wet granulation comprises mixing of intragranular ingredients into a pre-blend, addition of liquid to the pre-blend for wetting of the pre-blend and formation of granules, milling for deagglomeration of granules, and drying and screening of the resulting granules. In certain embodiments, the method comprises making placebo layer blend comprising placebo layer granules and extragranular components; making active layer blend comprising active layer granules and extragranular components; making push layer blend comprising push layer granules and extragranular components; filling the placebo layer blend, followed by the active layer blend, and finally the push layer blend into a tablet dye; compressing the three blends into a trilayer tablet core; coating the trilayer tablet core with a semipermeable membrane coat; drilling of an orifice in the semipermeable membrane coat and facing the placebo layer such that placebo layer is in fluid communication with the orifice, and optionally coating the resulting tablet with a cosmetic coat.

In certain embodiments, the placebo layer comprises a placebo layer blend comprising placebo layer granules and extragranular excipients. In certain embodiments, the placebo layer granules comprise a polyethylene oxide polymer with an average molecular weight of from about 300,000 Da to about 900,000 Da (preferably from about 400,0000 Da to about 900,0000 Da, most preferably from about 600,000 Da to about 900,000 Da), a binder, an osmogen, a stabilizer, and a color pigment. In certain embodiments, granules further include a wicking agent. In certain embodiments, the presence of stabilizer, osmogen and/or wicking agent is optional. In certain embodiments, glidant and lubricant are present as extragranular excipients in the placebo layer blend.

In certain embodiments, active layer blend comprises active layer granules and extragranular excipients. In certain embodiments, the active layer granules comprise armodafinil/modafinil or a pharmaceutically acceptable salt thereof, a polyethylene oxide polymer with an average molecular weight of from about 100,000 Da to about 300, 000 Da, a binder, a surfactant, an osmogen, a stabilizer, and a color pigment. In certain embodiments, granules further include a wicking agent. In certain embodiments, presence of surfactant, osmogen, and/or wicking agent is optional. In certain embodiments, glidant and lubricant are present as extragranular excipients in the active layer blend.

In certain embodiments, the push layer blend comprises push layer granules and extragranular excipients. In certain embodiments, the push layer granules comprise a polyethylene oxide polymer with an average molecular weight of ≥1M Da, a binder, an osmogen, a stabilizer, and a color pigment. In certain embodiments, presence of stabilizer and/or color pigment is optional.

In certain embodiments, glidant and lubricant are present as extragranular excipients in the push layer blend.

In certain embodiments, the three blends are filled in a tablet dye in the following order: placebo layer blend, the active layer blend, and the push layer blend, and compressed into a trilayer tablet core. The resulting tablet core is coated with a semipermeable membrane coat followed by drilling of an orifice in the coating, and optionally coating the resulting tablet with a cosmetic coat.

In certain embodiments, the exemplary clinical situation described herein involves sleep disorder. In certain embodiments, compositions of the disclosure are used for treating sleep disorders. In certain embodiments, treatment of a sleep disorder comprises improving early morning wakefulness in adult patients with excessive sleepiness associated with obstructive sleep apnea (OSA), narcolepsy, shift work disorder (SWD), and idiopathic hypersomnolence. In certain embodiments, the clinical situation being treated is idiopathic hypersomnolence. involving sleep inertia/sleep drunkenness, a condition involving extreme or prolonged difficulty fully awakening and getting out of bed in the morning, a transitional state between sleep and wake marked by impaired performance, reduced vigilance, and desire to return to sleep. In certain embodiments, clinical situation being treated involves excessive daytime sleepiness, fragmented sleep at night, and cataplexy, a condition showing sudden episodes of muscle paralysis.

6.4. Features of the Dosage Form

The present disclosure provides delayed release compositions of a drug, e.g., armodafinil/modafinil or a pharmaceutically acceptable salt thereof, wherein the compositions can be programmed to release the drug at a desired time and for a desired duration, e.g., at a rhythm that matches the requirements for treatment in a sleep/wake cycle, with complete drug recovery at the end of the dosing period. The compositions of the disclosure can be programmed to control lag time associated with the delay period and release the drug, e.g., armodafinil/modafinil or a pharmaceutically acceptable salt thereof, at a desired rate after the delay period. In certain embodiments, the osmotic-controlled oral compositions are programmed to provide a lag time of at least about 4, 5, 6, 7, 8, 9, 10, 11, 12 hours, or intermediate time periods within the range. The compositions of the disclosure are suitable for oral administration and provide pH-independent drug release at an osmotically determined rate, even as the dosage form transits the gastrointestinal (GI) tract and encounters variable hydrodynamic environments of the GI (gastrointestinal) tract, as well as microenvironments with reduced fluid content and significantly different pH values. In certain embodiments, the oral compositions of the disclosure provide delayed release of the drug, with minimum variability in lag time in response to varying pH, fluid content and hydrodynamic conditions of a dissolution medium or the human GI tract. In certain embodiments, the minimal variability in lag time comprises variability of not more than 30%, not more than 29%, not more than 28%, not more than 27%, not more than 26%, not more than 25%, not more than 24%, not more than 23%, not more than 22%, not more than 21%, not more than 20%, not more than 19%, not more than 18%, not more than 17%, not more than 16%, not more than 15%, not more than 14%, not more than 13%, not more than 12%, not more than 11%, not more than 10%, not more than 9%, not more than 8%, not more than 7%, not more than 6%, not more than 5%, not more than 4%, not more than 3%, not more than 2%, not more than 1%, or any intermediate values therein, with variations in pH, presence or absence of food, gastric motility, or viscosity of dissolution medium.

In certain embodiments, the timing of administration of the composition (e.g., in the evening) is titrated to optimize the tolerability and efficacy of the dose, as seen during, e.g., the next morning and throughout the day. In certain embodiments, the delayed release compositions of the disclosure comprising armodafinil/modafinil or a pharmaceutically acceptable salt thereof are programmed to provide drug release as follows: a lag time of at least about, e.g., 6-8 hours, and release of the drug with at least 70% drug recovery in about 4-10 hours after the lag time. In certain embodiments, the compositions of the disclosure are programmed to reduce/minimize insomnia by limiting drug (e.g., armodafinil/modafinil or a pharmaceutically acceptable salt thereof) plasma concentration during the lag time to less than about 20% of $C_{max}$.

In certain embodiments, the compositions of the disclosure are programmed to obtain a desired lag time by adjusting the composition of the placebo layer and/or the push layer, e.g., the amount and/or molecular weight/grade of the polyethylene oxide polymer (e.g., POLYOX®) in the placebo layer and/or the push layer. In certain embodiments, the compositions of the disclosure are programmed to obtain a desired lag time by adjusting the coating composition of the semipermeable membrane, and/or the coating weight gain of the semipermeable membrane.

In certain embodiments, the lag time depends upon amount and/or molecular weight of the polyethylene oxide polymer in the placebo layer. In certain embodiments, the placebo layer provides a desired lag time by delaying the release of the active pharmaceutical ingredient/drug in the environment of use. In certain embodiments, the lag time depends upon the amount/volume of the placebo layer that must be displaced by the expanding push layer. In certain embodiments, the lag time depends upon the viscosity of the placebo layer in aqueous medium.

In certain embodiments, viscosity of placebo layer in aqueous medium depends upon the average molecular weight of the polyethylene oxide polymer present in the placebo layer. In certain embodiments, the viscosity of the placebo layer in aqueous medium increases with increasing average molecular weight of the polyethylene oxide polymer present in the placebo layer. In certain embodiments, the lag time increases with increasing the molecular weight/grade of the polyethylene oxide polymer present in the placebo layer. In certain embodiments, the volume of the placebo layer depends upon the amount of polyethylene oxide polymer present in the placebo layer.

In certain embodiments, the lag time depends upon the average molecular weight of the polyethylene oxide polymer present in the placebo layer and viscosity of the placebo layer in aqueous medium.

In certain embodiments, the average molecular weight of the polyethylene oxide polymer present in the placebo layer is higher than the average molecular weight of the polyethylene oxide polymer present in the active layer, such that the viscosity of placebo layer in aqueous medium is higher than the viscosity of active layer in aqueous medium. In certain embodiments, the average molecular weight of the polyethylene oxide polymer present in the push layer is higher than average molecular weight of polyethylene oxide polymer in placebo layer, and the average molecular weight of the polyethylene oxide polymer present in the placebo layer is higher than the average molecular weight of polyethylene oxide polymer in active layer. In certain embodiments, the viscosity, in 1 wt % aqueous medium at 25° C., of the push layer is higher than the viscosity of the placebo layer, and the viscosity of placebo layer is higher than the viscosity of the active layer. In certain embodiments, the active layer has the lowest viscosity.

In certain embodiments, the average molecular weight of the polyethylene oxide polymer in the placebo layer should be at least about 300,000 Da, preferably from about 600,000 Da to about 900,000 Da, to provide a lag time of at least about 4 hours. In certain embodiments, the average molecular weight of the polyethylene oxide polymer present in the placebo layer should be higher than the average molecular weight of the polyethylene oxide polymer present in the active layer to provide a lag time of at least about 4 hours. In certain embodiments, on placing the composition in an aqueous medium, the polyethylene oxide polymer in the push layer swells to trigger the osmotic engine and push the active and placebo layers out of the dosage form through the orifice in the membrane, and high viscosity of the placebo layer as compared to the active layer, opposes the pressure exerted by the push layer and increases the lag time.

In certain embodiments, the presence of osmogen and/or wicking agent in the placebo layer help in imbibition and distribution of dissolution medium into the placebo layer.

In certain embodiments, the drug:polymer weight ratio in the active layer affects release rate and drug recovery. In certain embodiments, the presence of osmogen and/or wicking agent in the active layer help in imbibition and distribution of dissolution medium into the active layer.

In certain embodiments, the presence of an osmogen and/or wicking agent in the active layer increases release rate and improves drug recovery.

In certain embodiments, the push layer amount affects lag time and drug recovery. In certain embodiments, the lag time decreases with increase in the average molecular weight of the polyethylene oxide polymer in the push layer. In certain embodiments, higher average molecular weight of the polyethylene oxide polymer in the push layer increases swelling amount of the push layer with imbibed fluid/dissolution medium and increases the push on the active layer and the placebo layer, thereby reducing the lag time for drug release.

In certain embodiments, the amount of osmogen in the push layer affects lag time, release rate and drug recovery. In certain embodiments, increasing the amount of osmogen in the push layer increases fluid imbibition by the push layer, which leads to decreasing lag time due to faster swelling of the polyethylene oxide polymer in the push layer.

In certain embodiments, the ratio of cellulose acetate and polyethylene glycol in the semipermeable membrane affects lag time and drug recovery. In certain embodiments, increasing amount of cellulose acetate in the membrane increases lag time and reduces drug recovery from the membrane coated tablets.

In certain embodiments, the lag time and release rate of the osmotic-controlled oral compositions of the disclosure does not substantially depend upon the pH and viscosity of the dissolution medium.

In certain embodiments, the lag time does not change with changing hydrodynamics of the dissolution medium.

In certain embodiments, the size and number of orifices may affect % relative standard deviation (% RSD) among tablets.

6.5. Methods of Treatment

In certain embodiments, the compositions of the disclosure release armodafinil/modafinil or a pharmaceutically acceptable salt thereof at a rhythm that matches the human circadian rhythm regulating sleep-wake cycle.

In certain embodiments, the disclosure provides delayed release armodafinil/modafinil compositions providing treatment of reducing sleep inertia and improving wakefulness in adult patients with excessive sleepiness associated with obstructive sleep apnea (OSA), narcolepsy, shift work disorder (SWD), and idiopathic hypersomnolence. In certain embodiments, the treatment involves reducing sleep inertia/sleep drunkenness, a condition involving extreme or prolonged difficulty fully awakening and getting out of bed in the morning, a transitional state between sleep and wake marked by impaired performance, reduced vigilance, and desire to return to sleep. In certain embodiments, the treatment involves reducing excessive daytime sleepiness, fragmented sleep at night, and cataplexy, a condition showing sudden episodes of muscle paralysis.

In certain embodiments, the disclosure provides a method for treating excessive sleep disorder in patients suffering from narcolepsy, obstructive sleep apnea, shift work sleep disorders, or idiopathic hypersomnia, the method comprising orally administering to the patient, a composition providing delayed release of a therapeutically effective amount an active agent comprising armodafinil or a pharmaceutically acceptable salt thereof, the composition comprising a multilayer core and a semipermeable membrane containing an orifice and surrounding the core. The multilayer core comprises a placebo layer, an active layer, and a push layer, wherein the placebo layer comprises at least one polyethylene oxide polymer having an average molecular weight of from about 600,000 Da to about 900,000 Da; the active layer comprises an active agent comprising armodafinil or a pharmaceutically acceptable salt thereof, and at least one polyethylene oxide polymer having a molecular weight of from about 100,000 Da to about 300,000 Da; and the push layer comprises at least one polyethylene oxide polymer having an average molecular weight of greater than or equal to 1000,000 Da, and at least one osmogen. The layers in the multilayer core are placed in the following order: the placebo layer in fluid communication with the orifice in the semipermeable membrane; the active layer; and the push layer facing away from the orifice. Viscosities in aqueous medium at 25° C. for the three layers is as follows: viscosity of push layer >viscosity of placebo layer >viscosity of active layer. The osmogen in the push layer is present in an amount of from about 10 w % to about 60 wt. %, based on total weight of the push layer, and the composition provides a lag time of at least 4 hours during which the composition releases no more than 10% of the active agent, followed by release of the active agent.

In certain embodiments, the disclosure provides a method for treating excessive sleep disorder in patients suffering from narcolepsy.

In certain embodiments, the disclosure provides a method for treating excessive sleep disorder in patients suffering from obstructive sleep apnea.

In certain embodiments, the disclosure provides a method for treating excessive sleep disorder in patients suffering from shift work sleep disorders.

In certain embodiments, the disclosure provides a method for treating excessive sleep disorder in patients suffering from idiopathic hypersomnia.

In certain embodiments, the disclosure provides a method for improving early morning wakefulness in patients suffering from Narcolepsy, obstructive sleep apnea, shift work sleep disorders, or idiopathic hypersomnia, the method comprising orally administering to the patient, a composition providing delayed release of a therapeutically effective amount an active agent comprising armodafinil or a pharmaceutically acceptable salt thereof, the composition comprising a multilayer core and a semipermeable membrane containing an orifice and surrounding the core. The multilayer core comprises a placebo layer, an active layer, and a push layer, wherein the placebo layer comprises at least one polyethylene oxide polymer having an average molecular weight of from about 600,000 Da to about 900,000 Da; the active layer comprises an active agent comprising armodafinil or a pharmaceutically acceptable salt thereof, and at least one polyethylene oxide polymer having a molecular weight of from about 100,000 Da to about 300,000 Da; and the push layer comprises at least one polyethylene oxide polymer having an average molecular weight of greater than or equal to 1000,000 Da, and at least one osmogen. The layers in the multilayer core are placed in the following order: the placebo layer in fluid communication with the orifice in the semipermeable membrane; the active layer; and the push layer facing away from the orifice. Viscosities in aqueous medium at 25° C. for the three layers is as follows: viscosity of push layer >viscosity of placebo layer >viscosity of active layer. The osmogen in the push layer is present in an amount of from about 10 w % to about 60 wt. %, based on total weight of the push layer, and the composition provides a lag time of at least 4 hours during which the composition releases no more than 10% of the active agent, followed by release of the active agent.

In certain embodiments, the disclosure provides a method for improving early morning wakefulness in patients suffering from narcolepsy.

In certain embodiments, the disclosure provides a method improving early morning wakefulness in patients suffering from obstructive sleep apnea.

In certain embodiments, the disclosure provides a method for improving early morning wakefulness in patients suffering from shift work sleep disorders.

In certain embodiments, the disclosure provides a method for improving early morning wakefulness in patients suffering from idiopathic hypersomnia.

In certain embodiments, the disclosure provides a method for treating excessive sleep disorder and improving early morning wakefulness in patients suffering from narcolepsy, obstructive sleep apnea, shift work sleep disorders, or idiopathic hypersomnia, the method comprising orally administering to the patient, a composition providing delayed release of a therapeutically effective amount an active agent comprising armodafinil or a pharmaceutically acceptable salt thereof, the composition comprising a multilayer core and a semipermeable membrane containing an orifice and surrounding the core. The multilayer core comprises a placebo layer, an active layer, and a push layer, wherein the placebo layer comprises at least one polyethylene oxide polymer having an average molecular weight of from about 600,000 Da to about 900,000 Da; the active layer comprises an active agent comprising armodafinil or a pharmaceutically acceptable salt thereof, and at least one polyethylene oxide polymer having a molecular weight of from about 100,000 Da to about 300,000 Da; and the push layer comprises at least one polyethylene oxide polymer having an average molecular weight of greater than or equal to 1000,000 Da, and at least one osmogen. The layers in the multilayer core are placed in the following order: the placebo layer in fluid communication with the orifice in the semipermeable membrane; the active layer; and the push layer facing away from the orifice. Viscosities in aqueous medium for the three layers at 25° C. is in the following order: viscosity of the push layer >viscosity of the placebo layer >viscosity of the active layer. The osmogen in the push layer is present in an amount of from about 10 w % to about 60 wt. %, based on total weight of the push layer, and the composition provides a lag time of at least 4 hours during which the composition releases no more than 10% of the active agent, followed by release of the active agent.

In certain embodiments, the method comprises treating excessive sleep disorder and improving early morning wakefulness in patients suffering from narcolepsy.

In certain embodiments, the method comprises treating excessive sleep disorder and improving early morning wakefulness in patients suffering from obstructive sleep apnea.

In certain embodiments, the method comprises treating excessive sleep disorder and improving early morning wakefulness in patients suffering from shift work sleep disorders.

In certain embodiments, the method comprises treating excessive sleep disorder and improving early morning wakefulness in patients suffering from idiopathic hypersomnia.

In certain embodiments, the disclosure provides armodafinil/modafinil compositions providing improved patient compliance and convenience. The compositions provide clinical benefits of delivering armodafinil/modafinil or a pharmaceutically acceptable salt thereof in a delayed manner, independent of patient physiological factors, and food. In certain embodiments, the disclosed compositions provide a timed, prolonged therapeutic effect when taken once a day.

The armodafinil/modafinil compositions of the disclosure provide food-independent delayed release that can avoid early morning dosing of armodafinil/modafinil or a pharmaceutically acceptable salt thereof to patients suffering from excessive sleepiness associated with obstructive sleep apnea, narcolepsy, shift work disorder, and hyper somnolence. The compositions can be administered, with or without food, at night, before bedtime, e.g., about 8:00 pm (although other dosing times are contemplated), and provide delayed controlled release of the drug, e.g., armodafinil/modafinil.

In certain embodiments, the disclosure provides armodafinil compositions to improve wakefulness in adult patients with excessive sleepiness associated with obstructive sleep apnea, narcolepsy, or shift work disorder. In certain embodiments, the armodafinil compositions are administered at night to provide delayed release of armodafinil during the day. In certain embodiments, the compositions are administered whatever time of the day one retires for an extended period of sleep.

Typically, armodafinil/modafinil are dosed prior to beginning an early morning routine, with some time to onset of treatment effect after administration. Patients on such medications experience sleep inertia, which impairs ability to wake up and take medication. The compositions of the disclosure provide a convenient method of administration in that a single dose can be taken (typically in the evening prior to going to bed, or at whatever time of the day one retires for an extended period of sleep) and the release of drug is delayed for at least about 4 hours, e.g., about 6-12 hours, thereby avoiding sleep inertia.

The present disclosure provides compositions that can improve the symptoms of various sleep-wake disorders, including idiopathic hypersomnia, obstructive sleep apnea, and circadian rhythm shift work sleep disorders. Such compositions address the long-felt need of providing food-independent delayed release that can avoid burdensome early morning dosing of the drug to the patients. The compositions of the disclosure provide a desired lag time that is substantially independent of the presence or absence of food, type of food, pH, gastric emptying, gastric motility, and volume of fluid in the GI tract. The compositions can be administered, with or without food, at night, before bedtime (e.g., at about 8 pm), and provide delayed release of the active agent, e.g., armodafinil/modafinil or a pharmaceutically acceptable salt thereof.

In certain embodiments, the compositions of the disclosure provide minimal variability in lag time in various hydrodynamic conditions and pH (both conditions and regions) of the GI tract.

In certain embodiments, the timing of administration is titrated to optimize the tolerability and efficacy the next morning and throughout the day. In certain embodiments, the compositions of the disclosure avoid insomnia by releasing less than 20 wt % of armodafinil/modafinil or pharmaceutically acceptable salt thereof during the lag time, based on the maximum plasma concentration of the drug, e.g, Camx. In certain embodiments, the compositions of the disclosure limit the amount of armodafinil/modafinil or a pharmaceutically acceptable salt thereof in plasma to less than about 15 wt. %, less than about 10 wt. %, less than about 5 wt. %, less than about 4 wt. %, less than about 3 wt. %, less than about 2 wt. %, or less than about 1 wt. %, based on maximum plasma concentration of the drug ($C_{max}$).

In certain embodiments, maintenance of wakefulness test (MWT) is performed to measure an individual's ability to remain awake during the daytime in a darkened quiet environment.

6.6. Methods of Manufacture

In certain embodiments, the pull layer and the push layer in the multilayer compositions of the disclosure comprise granules made by wet granulation. In certain embodiments, wet granulation comprises mixing of intragranular ingredients into a pre-blend, addition of liquid to the pre-blend for wetting of the pre-blend and formation of granules, milling for deagglomeration of granules, and drying and screening of the resulting granules.

In certain embodiments, the placebo layer comprises a placebo layer blend comprising placebo layer granules and extragranular excipients. In certain embodiments, the placebo layer granules comprise a polyethylene oxide polymer with an average molecular weight of from about 300,000 Da to about 900,000 Da (preferably from about 600,0000 Da to about 900,0000 Da), a binder, an osmogen, a stabilizer, and a color pigment. In certain embodiments, granules further include a wicking agent. In certain embodiments, the presence of stabilizer, osmogen and/or wicking agent is optional. In certain embodiments, glidant and lubricant are present as extragranular excipients in the placebo layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 50:50 and about 99:1 by weight. In certain embodiments, granules are dried, milled, blended with extragranular excipients, and compressed into the placebo layer blend. In certain embodiments, the placebo layer is made by dry granulation/slugging. In certain embodiments, the placebo layer is made by direct compaction In certain embodiments, active layer blend comprises active layer granules and extragranular excipients. In certain embodiments, the active layer granules comprise armodafinil/modafinil or a pharmaceutically acceptable salt thereof, a polyethylene oxide polymer with an average molecular weight of from about 100,000 Da to about 300,000 Da, a binder, a surfactant, an osmogen, a stabilizer, and a color pigment. In certain embodiments, granules further include a wicking agent. In certain embodiments, presence of surfactant, osmogen, and/or wicking agent is optional. In certain embodiments, glidant and lubricant are present as extragranular excipients in the active layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 50:50 and about 99:1 by weight. In certain embodiments, granules are dried, milled, blended with extragranular excipients, and compressed into the active layer blend. In certain embodiments, the placebo layer is made by dry granulation/slugging. In certain embodiments, the placebo layer is made by direct compaction.

In certain embodiments, the push layer blend comprises push layer granules and extragranular excipients. In certain embodiments, the push layer granules comprise a polyethylene oxide polymer with an average molecular weight of greater than or equal to 1,000,000 Da, a binder, an osmogen, a stabilizer, and a color pigment. In certain embodiments, presence of stabilizer and/or color pigment is optional.

In certain embodiments, glidant and lubricant are present as extragranular excipients in the push layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 50:50 and about 99:1 by weight.

In certain embodiments, granules are dried, milled, blended with extragranular excipients, and compressed into the push layer blend. In certain embodiments, the push layer is made by dry granulation/slugging. In certain embodiments, the push layer is made by direct compaction.

In certain embodiments, wet granulation can be low shear, high shear, or fluid bed granulation.

In certain embodiments, the fluid bed granulation comprises top spray granulation or rotor granulation.

In certain embodiments, the placebo layer blend, the active layer blend, and the push layer blend are filled and compressed sequentially into a tablet dye and finally compressed into a vertically compressed trilayer tablet core. The resulting tablet core is coated with a semipermeable membrane coat followed by laser drilling of an orifice in the coating, and optionally coating the resulting tablet with a cosmetic coat. In certain embodiments, the semipermeable membrane coat includes a water-soluble pore former.

In certain embodiments, the water-soluble pore former is a water-soluble plasticizer, e.g., polyethylene glycol (sold under the trade names PEG 400, PEG 1000, PEG 1450, PEG 3350). In certain embodiments, coating solvents used for coating comprise, but are not limited to, methylene chloride, carbon tetra chloride, acetone, methanol, ethanol, water, and/or any mixtures thereof. In certain embodiments, the coating solvent is a mixture of acetone and water. In certain embodiments, the acetone:water weight ratio is between 70:30 and 95:5. In certain embodiments, the acetone:water weight ratio is about 80:20, about 85:15, about 90:10, about 95:5, or any intermediate values therein. In certain embodiments, the solvents used for coating the semipermeable membrane include a mixture of acetone and water, wherein the film porosity increases with increasing water content.

In certain embodiments, the disclosure provides making a multilayered tablet core for providing delayed release of armodafinil/modafinil or a pharmaceutically acceptable salt thereof. The multilayered tablet core comprises a push layer and a pull layer. The pull layer comprises granules made by wet granulation or roller compaction, and the push layer comprises granules made by wet granulation or direct compaction/slugging. In certain embodiments, the pull layer comprises an active layer and a placebo layer.

In certain embodiments, the trilayer tablet core is coated with a semipermeable membrane. In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the surrounding fluid into the core, and not too small to build hydrostatic pressure within the core.

In certain embodiments, the orifice is made via manual or laser drilling. In certain embodiments, the optimum orifice diameter is less than about 2.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

In certain embodiments, the compositions of the disclosure include a surfactant to improve the solubility of armodafinil/modafinil or a pharmaceutically acceptable salt thereof. In certain embodiments, the surfactant comprises, one or more of esters of fatty acids; sorbitan fatty acid esters ethoxylated with from about 2 to about 30 moles of ethylene oxide; polyethylene glycol fatty acid esters; polyethylene glycol esters and polyethylene glycol ethers; and polyethoxylated carboxylic acids, PEG-7 hydrogenated castor oil, and PEG-30 dipolyhydroxystearate; block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; and polyoxyl 40 stearate, and any combinations thereof.

7. EXAMPLES

The following examples illustrate the disclosure in a nonlimiting manner. Unless indicated to the contrary, the numerical parameters set forth herein can vary depending upon the desired properties sought to be obtained by the present disclosure.

Example 1: Preparation of Delayed Release Armodafinil Tablet Compositions

The present Example provides various formulations for delayed release armodafinil tablets as outlined in Table 1, Table 2, and Table 3. Twelve different tablets were prepared.

TABLE 1

Delayed Release Armodafinil Tablets

| Composition | Tablet 1 mg/dose | Tablet 2 mg/dose | Tablet 3 mg/dose | Tablet 4 mg/dose |
|---|---|---|---|---|
| Placebo layer | | | | |
| Polyethylene oxide (sold under the trademark POLYOX ® WSR 205) | 123.0 | 164.0 | 205.0 | 164.0 |
| Sodium Chloride | 18.0 | 24.0 | 30.0 | 24.0 |
| Red Pigment (PB1595) | 0.06 | 0.08 | 0.10 | 0.08 |
| Butylated Hydroxy Toluene (BHT) | 0.20 | 0.27 | 0.33 | 0.27 |
| Povidone, USP | 6.75 | 9.0 | 11.25 | 9.0 |
| Colloidal Silicon Dioxide, NF | 0.75 | 1.0 | 1.25 | 1.0 |
| Stearic Acid, NF | 1.24 | 1.65 | 2.07 | 1.65 |
| Total Placebo layer Weight | 150.0 | 200.0 | 250.0 | 200.0 |
| Active layer | | | | |
| Armodafinil | 250.0 | 250.0 | 250.0 | 250.0 |
| Polyethylene oxide (sold under the trademark POLYOX ® WSR N80) | 96.0 | 96.0 | 96.0 | 96.0 |
| Crospovidone, NF | 20.0 | 20.0 | 20.0 | 20.0 |
| Sodium Chloride | 30.0 | 30.0 | 30.0 | 30.0 |
| Povidone, NF | 4.0 | 4.0 | 4.0 | 4.0 |
| Stearic Acid | 5.0 | 5.0 | 5.0 | 5.0 |
| Docusate Sodium | 10.0 | 10.0 | 10.0 | 10.0 |
| Total Active layer Weight | 415.0 | 415.0 | 415.0 | 415.0 |
| Push Layer | | | | |
| Polyethylene oxide (sold under the trademark POLYOX ® WSR Coagulant) | 140.0 | 140.0 | 140.0 | 105.0 |
| Sodium chloride | 37.0 | 37.0 | 37.0 | 27.75 |
| Red Pigment | 2.0 | 2.0 | 2.0 | 1.5 |
| Butylated hydroxytoluene (BHT) | 19.0 | 19.0 | 19.0 | 14.25 |
| Povidone, USP | 0.3 | 0.3 | 0.3 | 0.225 |
| Colloidal Silicon Dioxide, NF | 0.7 | 0.7 | 0.7 | 0.525 |
| Stearic Acid, NF | 1.0 | 1.0 | 1.0 | 0.75 |
| Total Push layer Weight | 200.0 | 200.0 | 200.0 | 150.0 |
| Tablet Core Weight | 765.0 | 815.0 | 865.0 | 765.0 |

TABLE 1-continued

| Delayed Release Armodafinil Tablets | | | | |
|---|---|---|---|---|
| Composition | Tablet 1 mg/dose | Tablet 2 mg/dose | Tablet 3 mg/dose | Tablet 4 mg/dose |
| Functional Coating Layer | | | | |
| OPADRY CA Clear (500F190004) | 38.35 | 40.75 | 43.25 | 38.25 |
| Final tablet Weight | 803.25 | 855.75 | 908.25 | 803.25 |

TABLE 2

| Delayed Release Armodafinil Tablets | | | | |
|---|---|---|---|---|
| Composition | Tablet 5 mg/dose | Tablet 6 mg/dose | Tablet 7 mg/dose | Tablet 8 mg/dose |
| Placebo layer | | | | |
| Polyethylene oxide (sold under the trademark POLYOX ® WSR 205) | 205.0 | 246.0 | 287.0 | 287.0 |
| Sodium Chloride | 30.0 | 36.0 | 42.0 | 42.0 |
| Red Pigment (PB1595) | 0.10 | 0.12 | 0.14 | 0.14 |
| Butylated Hydroxy Toluene (BHT) | 0.33 | 0.40 | 0.472 | 0.472 |
| Povidone, USP | 11.25 | 13.50 | 15.75 | 15.75 |
| Colloidal Silicon Dioxide, NF | 1.25 | 1.50 | 1.75 | 1.75 |
| Stearic Acid, NF | 2.07 | 2.48 | 2.88 | 2.88 |
| Total Placebo layer Weight | 250.0 | 300.0 | 350.0 | 350.0 |
| Active layer | | | | |
| Armodafinil | 250.0 | 250.0 | 250.0 | 250.0 |
| Polyethylene oxide (sold under the trademark POLYOX ® WSR N80) | 96.0 | 96.0 | 96.0 | 96.0 |
| Crospovidone, NF | 20.0 | 20.0 | 20.0 | 20.0 |
| Sodium Chloride | 30.0 | 30.0 | 30.0 | 30.0 |
| Povidone, NF | 4.0 | 4.0 | 4.0 | 4.0 |
| Stearic Acid | 5.0 | 5.0 | 5.0 | 5.0 |
| Docusate Sodium | 10.0 | 10.0 | 10.0 | 10.0 |
| Total Active layer Weight | 415.0 | 415.0 | 415.0 | 415.0 |
| Push Layer | | | | |
| Polyethylene oxide (sold under the trademark POLYOX ® WSR Coagulant) | 105.0 | 105.0 | 105.0 | 140.0 |
| Sodium chloride | 27.75 | 27.75 | 27.75 | 37.0 |
| Red Pigment | 1.5 | 1.5 | 1.5 | 2.0 |
| Butylated hydroxytoluene (BHT) | 14.25 | 14.25 | 14.25 | 19.0 |
| Povidone, USP | 0.225 | 0.225 | 0.225 | 0.3 |
| Colloidal Silicon Dioxide, NF | 0.525 | 0.525 | 0.525 | 0.7 |
| Stearic Acid, NF | 0.75 | 0.75 | 0.75 | 1.0 |
| Total Push layer Weight | 150.0 | 150.0 | 150.0 | 200.0 |
| Tablet Core Weight | 815.0 | 865.0 | 915.0 | 965.0 |
| Functional Coating Layer | | | | |
| OPADRY CA Clear (500F190004) | 40.75 | 43.25 | 45.75 | 48.25 |
| Final tablet Weight | 855.75 | 908.25 | 960.75 | 1013.3 |

TABLE 3

| Delayed Release Armodafinil Tablets | | | | |
|---|---|---|---|---|
| Composition | Tablet 8 mg/dose | Tablet 10 mg/dose | Tablet 11 mg/dose | Tablet 12 mg/dose |
| Placebo layer | | | | |
| Polyethylene oxide (sold under the trademark POLYOX ® WSR 1105) | 246.0 | 184.5 | 142.0 | 142.0 |
| Sodium Chloride | 36.0 | 27.0 | 35.0 | 35.0 |
| Red Pigment (PB1595) | 0.12 | 0.09 | 2.4 | 2.4 |
| Butylated Hydroxy Toluene (BHT) | 0.405 | 0.4304 | 0.3 | 0.3 |
| Povidone, USP | 13.5 | 10.13 | 18.5 | 18.5 |
| Colloidal Silicon Dioxide, NF | 1.50 | 1.125 | 0.5 | 0.5 |
| Stearic Acid, NF | 2.475 | 1.856 | 0.8 | 0.8 |
| Total Placebo layer Weight | 300.0 | 225.0 | 200.0 | 200.0 |
| Armodafinil | 250.0 | 250.0 | 250.0 | 250.0 |
| Polyethylene oxide (sold under the trademark POLYOX ® WSR N80) | 96.0 | 96.0 | 96.0 | 96.0 |
| Crospovidone, NF | 34.45 | 34.45 | 34.40 | 34.40 |
| Sodium Chloride | 14.98 | 14.98 | 15.0 | 15.0 |
| Povidone, NF | 4.0 | 4.0 | 4.0 | 4.0 |
| Colloidal Silicon Dioxide, NF | 0.83 | 0.83 | 0.8 | 0.8 |
| Stearic Acid | 4.19 | 4.19 | 4.2 | 4.2 |
| Butylated Hydroxy Toluene (BHT) | | | 0.6 | 0.6 |
| Docusate Sodium | 10.0 | 10.0 | 20.0 | 20.0 |
| Total Active layer Weight | 415.0 | 415.0 | 425.0 | 425.0 |
| Polyethylene oxide (sold under the trademark POLYOX ® WSR Coagulant) | 140.8 | 140.8 | 246.0 | 246.0 |
| Sodium chloride | 35.20 | 35.20 | 36.9 | 36.9 |
| Red Pigment | 2.4 | 2.4 | 0.12 | 0.12 |
| Butylated hydroxytoluene (BHT) | 0.32 | 0.32 | 0.36 | 0.36 |
| Povidone, USP | 19.20 | 19.20 | 13.02 | 13.02 |
| Colloidal Silicon Dioxide, NF | 1.12 | 1.12 | 1.20 | 1.20 |
| Stearic Acid, NF | 0.96 | 0.96 | 2.4 | 2.4 |
| Total Push layer Weight | 200.0 | 200.0 | 300.0 | 300.0 |
| Tablet Core Weight | 915.0 | 840.0 | 925.0 | 925.0 |
| OPADRY CA Clear (500F190004) | 45.75 | 42.0 | 55.5 | 74.0 |
| Final tablet Weight | 960.8 | 882.0 | 980.5 | 999.0 |

Manufacturing Procedure:

Separate blends of placebo layer, active layer, and push layer were made as per Tables 1-3, using the following manufacturing procedure.

1. Preparation of Placebo Layer Blend:

a). Polyethylene oxide, sodium chloride, red pigment, and butylated hydroxytoluene were mixed for about 2 minutes in a high shear granulator.

b). Povidone was added to a hydroalcoholic mixture to obtain a hydroalcoholic solution of povidone.

c). Hydroalcoholic solution of povidone from step b) was added to the mixture from step a) while mixing to obtain a suitable granule size.

d) Wet granules from step c) were further milled, screened with screen #2A045R03137, and dried in a forced air oven at 40° C., until less than 1% loss on drying (LOD) is attained.

e) The granules from step d) were screened through #20 mesh screen and transferred to a V-blender.

f) Colloidal silicon dioxide was added to the V-blender and further mixed for about 10 minutes.

g) Stearic acid was passed through #30 mesh screen and added to the mixture in V-blender from step f) and further mixed for about 3 minutes.

2. Preparation of Active Layer Blend:

a) Armodafinil, polyethylene oxide, crospovidone, and sodium chloride, were added to a high shear granulator and mixed for about 5 minutes with chopper on position.

b) Povidone was added to a hydroalcoholic mixture to obtain a hydroalcoholic solution of povidone.

c) Hydroalcoholic solution of povidone from step b) was added to the mixture from step a) while mixing to obtain a suitable granule size.

d) Wet granules from step c) were further milled, screened with screen #2A045R03137, and dried in a forced air oven at 40° C., until less than 1% LOD is attained.

e) The granules from step d) were screened through #20 mesh screen and transferred to a V-blender.

f) Docusate sodium was added to the V-blender from step e) and further mixed for about 10 minutes.

g) Stearic acid was passed through #30 mesh screen and added to the mixture in V-blender from step f) and further mixed for about 3 minutes.

3. Preparation of Push Layer Blend a) Polyethylene oxide, sodium chloride, red pigment, and butylated hydroxytoluene were added to a high shear granulator and mixed for about 2 minutes with chopper on position.

b) Povidone was added to a hydroalcoholic mixture to obtain a hydroalcoholic solution of povidone.

c) Hydroalcoholic solution of povidone from step b) was added to the mixture from step a) while mixing to obtain a suitable granule size.

d) Wet granules from step c) were dried in a forced air oven at 40° C., until less than 1% LOD is attained.

e) The granules from step d) were screened through #25 mesh screen and transferred to a V-blender.

f) Colloidal silicon dioxide was added to the V-blender and further mixed for about 10 minutes.

g) Stearic acid was passed through #30 mesh screen and added to the mixture in V-blender from step f) and further mixed for about 3 minutes.

4. Compression:

The blends from steps 1, 2, and 3 were introduced into a tablet press and pressed in the following sequential order: placebo layer blend, followed by active layer blend, and finally push layer blend. The tablet press comprising the three blend layers was finally pressed to provide a vertically compressed trilayer tablet core.

5. Coating:

a) Coating suspension was prepared by dissolving OPADRY CA Clear into acetone-water mixture.

b) Compressed tablets from step 4 were transferred to a suitably sized coating pan and sprayed with the coating suspension from step a) to achieve desired coating weight gain.

6. Laser Drilling:

Coated tablets from step 5) were laser drilled with a 0.4 mm size orifice on placebo layer side of the coating/membrane such that orifice is in fluid communication with the placebo layer.

Example 2: In Vitro Dissolution Using USP Apparatus II (Sinkers)

Trilayer armodafinil Tablets 1, 11, and 12 were tested for dissolution in about 900 ml of about pH 6.8 buffer for up to 24 hours, using USP Apparatus II (Paddle), at 50 rpm and 37° C.

Percentage dissolution of the tablet was measured at 2, 4, 6, 8, 10, 12, 14, 16, 18, 20, 22, and 24 hours. FIG. 2 shows that tablet 1 provides a lag time of at least about 6 hours during which not more than 10% of armodafinil is released.

FIG. 3 shows that Tablets 11 (6% coating wt. gain) and 12 (8% coating wt. gain) provide a lag time of at least about 6 hours during which not more than 10% of armodafinil is released. The figure further demonstrates that Tablet 11 with 6% coating wt. gain provided faster release compared to Tablet 12 with 8% coating wt. gain.

The present disclosure is not to be limited in scope by the specific embodiments described herein. Indeed, various modifications of the disclosure in addition to those described herein will become apparent to those skilled in the art from the foregoing description. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions, and protocols are cited throughout this application, the disclosures of which are incorporated herein by reference in their entireties for all purposes.

The invention claimed is:

1. A delayed release composition comprising:

a) a vertically compressed multilayer core comprising a placebo layer, an active layer, and a push layer, wherein:

(i) the placebo layer comprises at least one polyethylene oxide polymer having a weight average molecular weight of from about 400,000 Da to about 900,000 Da, (ii) the active layer comprises an active agent comprising armodafinil or a pharmaceutically acceptable salt thereof, and at least one polyethylene oxide polymer having a weight average molecular weight of from about 100,000 Da to about 300,000 Da, (iii) the push layer comprises at least one polyethylene oxide polymer having a weight average molecular weight of greater than or equal to 1,000,000 Da; and b) a semipermeable membrane containing an orifice and surrounding the multilayer core, and wherein the layers in the multilayer core are placed in the following order: the placebo layer facing the orifice in the semipermeable membrane; the active layer; and the push layer facing away from the orifice.

2. The composition of claim 1, wherein the push layer further comprises an osmogen in an amount from about 10 wt % to about 60 wt %, based on total weight of the push layer.

3. The composition of claim 1, wherein the composition provides a lag time of at least about 4 hours, during which the composition releases no more than 10 wt. % of the active agent.

4. The composition of claim 1, wherein the semipermeable membrane is present in an amount of from about 1 wt. % to about 30 wt. % coating weight gain, based on the total weight of the uncoated multilayer core.

5. The composition of claim 1, wherein the semipermeable membrane comprises at least one water-insoluble polymer and at least one plasticizer.

6. The composition of claim 5, wherein the plasticizer is selected from the group consisting of polyethylene glycols, triethyl citrate, triacetin, diethyl tartrate, dibutyl sebacate, and combinations thereof.

7. The composition of claim 5, wherein the water-insoluble polymer is selected from the group consisting of cellulose acetate, cellulose acetate butyrate, and cellulose triacetate.

8. The composition of claim 1, wherein the polyethylene oxide polymer in the push layer has a weight average molecular weight of about 1000,000 Da, about 2000,000 Da, about 4000,000 Da, about 5000,000 Da, about 7000,000 Da, or intermediate values therein.

9. The composition of claim 1, wherein the active layer comprises a weight ratio of the active agent:polyethylene oxide polymer of from about 50:50 to about 95:5.

10. The composition of claim 1, wherein each of the push layer, the placebo layer, and the active layer exhibit a viscosity, measured using Brookfield viscometer, in 1 wt % aqueous solution at 25° C., wherein the viscosity of the push layer is higher than the viscosity of the placebo layer, and the viscosity of the placebo layer is higher than the viscosity of the active layer.

11. A method for treating excessive sleep disorder in patients suffering from narcolepsy, obstructive sleep apnea, shift work sleep disorders, or idiopathic hypersomnia, the method comprising orally administering to the patient a delayed release composition comprising:

a) a vertically compressed multilayer core comprising a placebo layer, an active layer, and a push layer, wherein:

(i) the placebo layer comprises at least one polyethylene oxide polymer having a weight average molecular weight of from about 400,000 Da to about 900,000 Da, (ii) the active layer comprises an active agent comprising armodafinil or a pharmaceutically acceptable salt thereof, and at least one polyethylene oxide polymer having a weight average molecular weight of from about 100,000 Da to about 300,000 Da, (iii) the push layer comprises at least one polyethylene oxide polymer having a weight average molecular weight of greater than or equal to 1,000,000 Da; and b) a semipermeable membrane comprising an orifice and surrounding the multilayer core, and wherein the layers in the multilayer core are placed in the following order: the placebo layer facing the orifice in the semipermeable membrane; the active layer; and the push layer facing away from the orifice.

12. The method of claim 11, wherein each of the push layer, the placebo layer, and the active layer exhibit a viscosity, measured using Brookfield viscometer, in 1 wt % aqueous solution at 25° C., wherein the viscosity of the push layer is higher than the viscosity of the placebo layer, and the viscosity of the placebo layer is higher than the viscosity of the active layer.

13. A method for treating excessive sleep disorder and improving early morning wakefulness in patients suffering from narcolepsy, obstructive sleep apnea, shift work sleep disorders, or idiopathic hypersomnia, the method comprising orally administering to the patient a delayed release composition comprising:

a) a vertically compressed multilayer core comprising a placebo layer, an active layer, and a push layer, wherein:

(i) the placebo layer comprises at least one polyethylene oxide polymer having a weight average molecular weight of from about 400,000 Da to about 900,000 Da, (ii) the active layer comprises an active agent comprising armodafinil or a pharmaceutically acceptable salt thereof, and at least one polyethylene oxide polymer having a weight average molecular weight of from about 100,000 Da to about 300,000 Da, (iii) the push layer comprises at least one polyethylene oxide polymer having a weight average molecular weight of greater than or equal to 1,000,000 Da, and b) a semipermeable membrane comprising an orifice and surrounding the multilayer core, and wherein the layers in the multilayer core are placed in the following order: the placebo layer facing the orifice in the semipermeable membrane; the active layer; and the push layer facing away from the orifice.

14. The method of claim 13, wherein each of the push layer, the placebo layer, and the active layer exhibit a viscosity, measured using Brookfield viscometer, in 1 wt % aqueous solution at 25° C., wherein the viscosity of the push layer is higher than the viscosity of the placebo layer, and viscosity of the placebo layer is higher than the viscosity of the active layer.

15. A method for making a delayed release composition comprising a multilayer core comprising a placebo layer comprising a placebo layer blend; an active layer comprising an active layer blend; and a push layer comprising a push layer blend; and a semipermeable membrane covering at least a portion of the multilayer core and comprising at least one orifice; the method comprising:

(i) making a placebo layer blend comprising at least one polyethylene oxide polymer having a weight average molecular weight of from about 400,000 Da to about 900,000 Da;

(ii) making an active layer blend comprising an active agent comprising armodafinil or a pharmaceutically acceptable salt thereof, and at least one polyethylene oxide polymer having a weight average molecular weight of from about 100,000 Da to about 300,000 Da;

(iii) making a push layer blend comprising at least one polyethylene oxide polymer having a weight average molecular weight of greater than or equal to 1,000,000 Da;

(iv) sequentially filling and compressing the placebo layer blend, followed by the active layer blend, and finally the push layer blend into a tablet dye; and finally compressing the three blends into a multilayer tablet core;

(v) coating the multilayer core with a semipermeable membrane coat; and (vi) laser drilling an orifice in the semipermeable membrane coat, wherein the layers in the multilayer core are placed in the following order: the placebo layer facing the orifice in the semipermeable membrane; the active layer; and the push layer facing away from the orifice.

16. The method of claim 15, wherein the placebo layer blend comprises placebo layer granules comprising the polyethylene oxide polymer with a weight average molecular weight of from about 400,0000 Da to about 900,0000 Da.

17. The method of claim 15, wherein the active layer blend comprises active layer granules comprising the polyethylene oxide polymer with a weight average molecular weight of from about 100,0000 Da to about 300,0000 Da.

18. The method of claim 16, wherein the push layer blend comprises push layer granules comprising the polyethylene oxide polymer with a weight average molecular weight of greater than or equal to 1000,000 Da.

* * * * *